(12) United States Patent
Garry et al.

(10) Patent No.: US 11,673,928 B2
(45) Date of Patent: Jun. 13, 2023

(54) GENETICALLY MODIFIED PIG CELLS WITH AN INACTIVATED ETV2 GENE

(71) Applicant: Regents of the University of Minnesota, Minneapolis, MN (US)

(72) Inventors: Daniel J. Garry, Eagan, MN (US); Mary G. Garry, Eagan, MN (US); Tara Rasmussen, Savage, MN (US); Naoko Koyano, Shoreview, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/554,585

(22) PCT Filed: Mar. 3, 2016

(86) PCT No.: PCT/US2016/020768
§ 371 (c)(1),
(2) Date: Aug. 30, 2017

(87) PCT Pub. No.: WO2016/141234
PCT Pub. Date: Sep. 9, 2016

(65) Prior Publication Data
US 2018/0037620 A1    Feb. 8, 2018

Related U.S. Application Data

(60) Provisional application No. 62/127,330, filed on Mar. 3, 2015.

(51) Int. Cl.
| | |
|---|---|
| *C12N 5/00* | (2006.01) |
| *C07K 14/47* | (2006.01) |
| *A01K 67/027* | (2006.01) |
| *C12N 5/073* | (2010.01) |
| *C12N 5/0735* | (2010.01) |
| *C12N 15/877* | (2010.01) |
| *C12N 15/09* | (2006.01) |

(52) U.S. Cl.
CPC ...... *C07K 14/4705* (2013.01); *A01K 67/0271* (2013.01); *A01K 67/0276* (2013.01); *C12N 5/0604* (2013.01); *C12N 5/0606* (2013.01); *C12N 15/09* (2013.01); *C12N 15/8778* (2013.01); *A01K 2207/15* (2013.01); *A01K 2217/075* (2013.01); *A01K 2227/108* (2013.01); *A01K 2267/025* (2013.01)

(58) Field of Classification Search
CPC .......... C12N 15/8778; A01K 2227/108; A01K 67/0276; A01K 67/0271
USPC ................. 800/8, 13–18; 435/325
See application file for complete search history.

(56) References Cited

U.S. PATENT DOCUMENTS

| | | |
|---|---|---|
| 5,994,619 A | 11/1999 | Stice et al. |
| 6,545,199 B1 | 4/2003 | Anderson et al. |
| 8,685,737 B2 | 4/2014 | Serber et al. |
| 9,446,076 B2 | 9/2016 | Gaussin et al. |
| 10,874,092 B2 | 12/2020 | Garry et al. |
| 10,897,880 B2 | 1/2021 | Garry et al. |
| 2005/0125853 A1 | 6/2005 | Parekh |
| 2006/0008451 A1 | 1/2006 | Cibelli et al. |
| 2006/0191029 A1 | 8/2006 | Gavin et al. |
| 2009/0288177 A1 | 11/2009 | Habu et al. |
| 2010/0107263 A1 | 4/2010 | Kerr et al. |
| 2010/0122360 A1 | 5/2010 | Nakauchi et al. |
| 2011/0258715 A1 | 10/2011 | Nakauchi et al. |
| 2011/0277047 A1 | 11/2011 | Bruggemann |
| 2012/0207744 A1 | 8/2012 | Mendlein et al. |
| 2014/0115728 A1 | 4/2014 | Tector |
| 2014/0186414 A1 | 7/2014 | Ingber et al. |
| 2015/0140658 A1 | 5/2015 | Kamp et al. |
| 2015/0168125 A1 | 6/2015 | Arieli et al. |
| 2016/0029604 A1 | 2/2016 | Fahrenkrug et al. |
| 2018/0177165 A1 | 6/2018 | Garry et al. |
| 2018/0177166 A1 | 6/2018 | Garry et al. |
| 2019/0133093 A1 | 5/2019 | Nakauchi et al. |

(Continued)

FOREIGN PATENT DOCUMENTS

| | | |
|---|---|---|
| CN | 1212009 A | 3/1999 |
| CN | 1241210 A | 1/2000 |
| CN | 102196722 A | 9/2011 |

(Continued)

OTHER PUBLICATIONS

Ferdous (PNAS, Jan. 20, 2009, vol. 106, No. 3, p. 814-819).*
Rassmussen (Development, 2011, vol. 138, p. 4812).*
Kataoka (Blood, Dec. 22, 2011, vol. 118, No. 26, p. 6975).*
Shi (J. Biol. Chem., Feb. 18, 2015, vol. 290, No. 15, p. 9614-9625).*
"U.S. Appl. No. 15/739,042, Preliminary Amendment filed Dec. 21, 2017", 9 pgs.

(Continued)

*Primary Examiner* — Michael C Wilson
(74) *Attorney, Agent, or Firm* — Schwegman Lundberg & Woessner, P.A.

(57) ABSTRACT

Described herein is a method for producing a chimeric non-human animal expressing a human ETV2 gene comprising: a) generating an ETV2 null non-human animal cell, wherein both copies of the non-human ETV2 gene carry a mutation that prevents production of functional ETV2 protein in said non-human animal; b) creating an ETV2 null non-human blastocyst by somatic cell nuclear transfer comprising fusing a nucleus from said ETV2 null non-human animal cell of a) into an enucleated non-human oocyte and activating said oocyte to divide so as to form an ETV2 null non-human blastocyst; c) introducing human stem cells into the ETV2 null non-human blastocyst of b); and d) implanting said blastocyst from c) into a pseudopregnant surrogate non-human animal to generate a chimeric non-human animal expressing human ETV2.

1 Claim, 15 Drawing Sheets

Specification includes a Sequence Listing.

(56) References Cited

U.S. PATENT DOCUMENTS

| | | | |
|---|---|---|---|
| 2021/0161110 | A1 | 6/2021 | Garry et al. |
| 2021/0169054 | A1 | 6/2021 | Garry et al. |

FOREIGN PATENT DOCUMENTS

| | | | |
|---|---|---|---|
| CN | 102438636 | A | 5/2012 |
| CN | 108024522 | A | 5/2018 |
| CN | 108125943 | A | 6/2018 |
| CN | 108472318 | A | 8/2018 |
| EP | 2258166 | A1 | 12/2010 |
| GB | 2475656 | A | 5/2011 |
| JP | 2010-515737 | A | 5/2010 |
| JP | 2014-533491 | A | 12/2014 |
| JP | 2018-506984 | A | 3/2018 |
| JP | 2018-522553 | A | 8/2018 |
| JP | 2018-523999 | A | 8/2018 |
| WO | WO-2004/004447 | A2 | 1/2004 |
| WO | WO-2008/102602 | A1 | 8/2008 |
| WO | WO-2015/168125 | A1 | 11/2015 |
| WO | WO-2016141234 | A1 | 9/2016 |
| WO | WO-2017/004367 | A1 | 1/2017 |
| WO | WO-2017/004388 | A1 | 1/2017 |
| WO | WO-2017/075276 | A2 | 5/2017 |

OTHER PUBLICATIONS

"U.S. Appl. No. 15/739,066, Preliminary Amendment filed Dec. 21, 2017", 9 pgs.

"Colombian Application Serial No. NC2018/0000859, Office Action dated Feb. 21, 2018", (w/ English Translation), 6 pgs.

"International Application Serial No. PCT/US2016/020768, International Preliminary Report on Patentability dated Sep. 14, 2017", 6 pgs.

"International Application Serial No. PCT/US2016/040378, International Preliminary Report on Patentability dated Jan. 11, 2018", 9 pgs.

"International Application Serial No. PCT/US2016/040378, International Search Report dated Oct. 26, 2016", 4 pgs.

"International Application Serial No. PCT/US2016/040378, Written Opinion dated Oct. 26, 2016", 7 pgs.

"International Application Serial No. PCT/US2016/040431, International Preliminary Report on Patentability dated Jan. 11, 2018", 9 pgs.

"International Application Serial No. PCT/US2016/040431, International Search Report dated Oct. 26, 2016", 4 pgs.

"International Application Serial No. PCT/US2016/040431, Written Opinion dated Oct. 26, 2016", 7 pgs.

"Japanese Application Serial No. 2017-546061, Written Amendment filed Dec. 1, 2017", (w/ English Translation of Amended Claims), 11 pgs.

"Vietnamese Application Serial No. 1-2017-03882, Office Action dated Dec. 4, 2017", (w/ English Translation), 2 pgs.

"Vietnamese Application Serial No. 1-2017-03882, Response filed Jan. 4, 2018 to Office Action dated Dec. 4, 2017", (w English Translation of Amended Claims), 9 pgs.

Beaucage, S., et al., "Deoxynucieoside Phosphoramidites—A New Class of Key Intermediate for Deoxypolynucleotide Synthesis", Tetrahedron Letters, 22, (1981), 1859-1862.

Berkes, C. A., et al., "MyoD and the transcriptional control of myogenesls", Seminars in Cell & Developmental Biology, 16, (2005), 585-595.

Bodmer, R., "The gene tinman is required for specification of the heart and visceral muscles in Drosophila", Development, 118(3), (1993), 719-729.

Bort, R., et al., "Hex homeobox gene controls the transition of the endoderm to a pseudostratified, cell emergent epithelium for liver bud development". Developmental Biology, 290(1), (2006), 44-56.

Bowlin, K. M., et al., "Kbibd5 is regulated by MyoD and restricted to the myogenic lineage", Differentiation, 86, (2013), 184-191.

Bruneau, Benoit G., et al., "A Murine Model of Holt-Oram Syndrome Defines Roles of the T-Box Transcription Factor Tbx5 in Cardiogenesis and Disease", Cell, 106(6), (Sep. 2001), 709-721.

Caprioli, A., et al., "Nkx2-5 Represses Gatal Gene Expression and Modulates the Cellular Fate of Cardiac Progenitors During Embryogenesis", Circulation, 123(15), (2011), 1633-1641.

Carlson, D. F et al., "Efficient TALEN-mediated gene knockout in liverstock", Proc. Natl. Acad. Sci., 109(43), (2012), 17382-17387.

Ferdous, A., "Nkx2-5 transactivates the Ets-related protein 71 gene and specifies an endothelial/endocardial fate in the developing embryo", Proc. Natl. Acad. Sci. USA, 106(3), (2009), 814-819.

Garry, D. J., et al., "A Common Progenitor at the Heart of Development", Cell, 127(6), (2006), 1101-1104.

Garry, D. J., et al., "Cardiac Regeneration—Self-Service at the Pump", Circulation Research, 95, (2004), 852-854.

Grefte S., Kuupers Mar, et al., "Myogenic capacity of muscle progenitor cells from head and limb muscles", Eur. J. Oral Sci., 120(1), (2012), 38-45.

Hiroi, Y., "Tbx5 associates with Nkx2-5 and synergistically promotes cardiomyocyte differentiation", Nat Genet., 28(3), (2001), 276-280.

Jansen, K. M., et al., "Molecular Control of Mammalian Myoblast Fusion", Methods in Molecular Biology, vol. 475—Cell Fusion: Overviews and Methods, (Feb. 2008), 115-133.

Kassar-Duchossoy, L., et al., "Mr4 determines skeletal muscle identity in Myf5:Myod double-mutant mice", Nature, 4317007), (2004), 466-471.

King, T. J., et al., "Embryo development and establishment of pregnancy after embryo transfer in pigs: Coping with limitations in the availability of viable embryos", Reproduction, 123(4), (2002), 507-515.

Kobayashi, Toshihiro, et al., "Generation of Rat Pancreas in Mouse by Interspecific Blastocyst Injection of Pluripotent Stem Cells", Cell, 142(5), (2010), 787-799.

Koyano-Nakagawa, Naoko, et al., "Etv2 is expressed in the yolk sac hematopoietic and endothelial progenitors and regulates Lmo2 gene expression", Stem Cells, 30(8), (2012), 1611-1623.

Kure-Bayashi, S., et al., "Successful implantation of in vitromatured, electo-activated oocytes in the pig", Theriogenology, 53(5), (2000), 1105-1119.

Latif, S., et al., "Transcriptional Pathways Direct Cardiac Development and Regeneration", Trends Cardiovasc Med., 16(7), (2006), 234-240.

Lewis, F. C., et al., "Porcine Sketal Muscke-Derived Multipotent $PW1^{pos}/Pax7^{neg}$ Interstitial cells: Isolation, Characterization, and Long-Term Culture", Stem Cells Transl Med, 3(6), (2014), 702-712.

Lyons, Ian, et al., "Myogenic and morphogenetic defects in the heart tubes of murine embryos lacking the homeo box gene Nkx2-5", Genes & Development, 9(13), (1995), 1654-1666.

Matsunari, Hitomi, et al., "Blastocyst complementation generates exogenic pancreas in vivo in apancreatic cloned pigs", Proc. Natl. Acad. Sci., 110(12), (2013), 4557-4562.

Matteucci, M. D., et al., "Synthesis of Deoxyoligonucleotides on a Polymer Support", J. Am. Chem. Soc., 103, (1981), 3185-3191.

McKarney, L. A., et al., "Myogenesls in Cultures ot Uniparental Mouse Embryonic Stem Cells: Differing Patterns of Expression of Myogenic Regulatory Factors", Int. J, Dev. Biol., 41, (1997), 485-490.

Nakano, Kazuaki, et al., "Generating Porcine Chimeras Using Inner Cell Mass Cells and Parthenogenetic Preimplantation Embryos", PLoS One, 8(4): e61900, (Apr. 2013), 1-10.

Niu, Yuyu, et al., "Generation of Gene-Modified Cynomolgus Monkey via Cas9/RNA-Mediated Gene Targeting in One-Cell Embryos", Cell 156, (Feb. 2014), 836-843.

Pasut, A., et al., "Chapter 3—Isolation of Muscle Stem Cells by Fluorescence Activated Cell Sorting Cytometry", DiMario, J. X., (ed.), Myogenesis: Methods Mol Biol., vol. 798, (2012), 53-64.

Rashid, Tamir, et al., "Revisiting the Flight of Icarus: Making Human Organs from PSCs with Large Animal Chimeras", Cell Stem Cell 15, (Oct. 2014), 406-409.

Rasmussen, T. L., et al., "Getting to the Heart of Myocardial Stem Cells and Cell Therapy", Circulation, 123, (2011), 1771-1779.

(56) References Cited

OTHER PUBLICATIONS

Rasmussen, T. L., et al., "Abstract 15450: Ets Related Protein 71 Regulates Cardiac Morphogenesis", Circulation, 122: A15450, (2010), 2 pgs.
Rasmussen, T. L et al., "Abstract 17036: Flk1 Mediated Activation of ER71 and Specification of Cardiovascular Lineages", Circulation, 124: A17036, (2011), 2 pgs.
Rasmussen, T. L., et al., "ER71 directs mesodermal fate decisions during embryogenesis". Development 138, (2011), 4801-4812.
Rasmussen, T. L., et al., "VEGF/Flk1 Signaling Cascade Transactivates Etv2 Gene Expression", PLoS One, 7(11): e50103, (Nov. 2012), 1-12.
Sabourin, L. A., et al., "The molecular regulation of myogenesis", Clin. Genet., 57, (2000), 16-25.
Shi, X., et al., "Cooperative interaction of Etv2 and Gata2 regulates the development of endothelial and hematopoietic lineages", Developmental Biology, 389(2), (2014), 208-218.
Shi, X., et al., "Muscle stem cells in development, regeneration, and disease", Genes & Development 20, (2006), 1692-1708.
Srivastava. D., et al., "Regulation of cardiac mesodermal and neural crest development by the bHLH transcription factor", Nat Gen., 16(2), (1997), 154-160.
Takeda, Kumiko, "Microinjection of serum-starved mitochondria derived from somatic cells affects parthenogenetic development of bovine and murine oocytes", Mitochondrion, 10(2), (Mar. 2010), 137-142.
Tan, Wenfang, et al., "Efficient nonmeiotic allele introgression in livestock using custom endonucleases", Proc. Natl. Acad. Sci., 110(41), (2013), 16526-16531.
Tapscott, S. J., et al., "The circuitry of a master switch: Myod and the regulation of skeletal muscle gene transcription", Development, 132(12), (2005), 2685-2695.
Te Pas, M. F., et al., "Biochemical pathways analysis of microarry results: regulation of myogenesis in pigs", BMC Dev. Bio., 7: 66, (2007), 1-15.
Usui, Jo-Ichi, et al., "Generation of Kidney from Pluripotent Stem Cells via Blastocyst Complementation", The American Journal of Pathology, 180(6), (Jun. 2012), 2417-2426.
Wang, Haoyi, et al., "One-Step Generation of Mice Carrying Mutations in Multiple Genes by CRISPR/Cas-Mediated Genome Engineering", Cell, 153, (2013), 910-913.
Woolf, A. D., et al., "Burden of major musculoskeletal conditions", Bulletin of the World Health Organization, 81(9), (2003), 646-656.
Wu, J., et al., "Generation of human organs in pigs via interspecies blastocyst complementation", Reprod Dorn Anim, 51 (Suppl. 2), 18-24.
Yamagishi, H., "The combinatorial activities of Nkx2.5 and dHAND are essential for cardiac ventricle formation", Developmental Biology, 239(2), (2001), 190-203.
Zhu, J., "In Vitro and In Vivo Developmental Competence of Ovuated and In Vitro Matured Porcine Oocytes Activated by Electrical Activation", Cloning Stem Cells, 5(4), (2003), 355-365.
"International Application Serial No. PCT/US16/20768, International Search Report dated Jul. 22, 2016", 3 pgs.
"International Application Serial No. PCT/US16/20768, Written Opinion dated Jul. 22, 2016", 4 pgs.
Shi, et al., "The Transcription Factor Mespl Interacts with cAMP-responsive Element Binding Protein 1 (Crebl) and Coactivates Ets Variant 2 (Etv2) Gene Expression", The Journal of Biological Chemistry, vol. 290, No. 15, (Feb. 18, 2015), 9614-9625 pgs.
Wareing, et al., "The Flk1-Cre-Mediated Deletion of ETV2 Defines Its Narrow Temporal Requirement During Embryonic Hematopoietic Development", Stem Cells, vol. 30, (Jun. 18, 2012), 1521-1531 pgs.
"Colombian Application Serial No. NC2018/0000859, Response filed Jun. 13, 2018 to Office Action dated Feb. 21, 2018", (w/ English Translation of Claims), 14 pgs.
"European Application Serial No. 16759528.9, Extended European Search Report dated Aug. 8, 2018", 8 pgs.
"European Application Serial No. 16818785.4, Response filed May 21, 2018 to Office Action dated Feb. 16, 2018", 5 pgs.

"European Application Serial No. 16818799.5, Response filed May 21, 2018 to Office Action dated Feb. 16, 2018", 5 pgs.
Lammerts Van Bueren, Kelly, et al., "Regulation of endothelial and hematopoietic development by the ETS transcription factor Etv2", Current Opinion in Hematology, 19(3), (Mar. 2012), 199-205.
Morita, Rimpei, et al., "ETS transcription factor ETV2 directly converts human fibroblasts into functional endothelial cells", Proceedings of the National Academy of Sciences, 112,(1), (Dec. 24, 2014), 160-165.
Swaminathan, Preethi, "Human Stem Cell Complementation in PITX3 Null Porcine Blastocysts: Lens Development", [Online]. Retrieved from the Internet: <URL: https://conservancy.unm.edu/bi tstream/handle/11299/185108/Swaminathan_umn_0130M_15713.pdf>, (Dec. 2014), 57 pages.
Wu, Jun, et al., "An alternative pluripotent state confers interspecies chimaeric competency", Nature, vol. 521, (2015), 23 pgs.
"Australian Application Serial No. 2016288196, First Statement of Proposed Amendments filed Jan. 31, 2018", 12 pgs.
"Canadian Application Serial No. 2,991,053, Voluntary Amendment filed Oct. 18, 2018", 13 pgs.
"Directive 98/44/EC of the European Parliament and of the Council of Jul. 6, 1998", Official Journal of the European Communities, (1998), 9 pgs.
"European Application Serial No. 16818799.5, Extended European Search Report dated Feb. 28, 2019", 10 pgs.
"European Application Serial No. 16860825.5, Supplementary European Search Report dated Apr. 9, 2019", 12 pgs.
"European Application Serial No. 16860830.5, Supplementary Partial European Search Report dated Apr. 16, 2019", 13 pgs.
"European Application Serial No. 16818785.4, Extended European Search Report dated Jan. 24, 2019", 7 pgs.
"Singaporean Patent Application No. 11201707151Y, Response filed Jan. 7, 2019 to Search Report and Written Opinion dated Aug. 6, 2018", (w/ English Claims), 42 pgs.
"Singaporean Patent Application No. 11201707151Y, Search Report and Written Opinion dated Aug. 6, 2018", 12 pgs.
Bouchard, Maxime, et al., "Nephric lineage specification by Pax2 and Pax8", Genes & Development, 16(22), (2002), 2958-2970.
Elcheva, Irina, et al., "Direct induction of hematoendothelial programs in human pluripotent stem cells by transcriptional regulators", Nature Communications, 5: 5372, (2014), 1-11.
Goto, Teppei, et al., "Generation of pluripotent stem cell-derived mouse kidneys in Sall1-targeted anephric rats", Nature Communications, 10, Article No. 451, (2019), 1-9.
Koyano-Nakagawa, N., et al., "Feedback Mechanisms Regulate Ets Variant 2 (Etv2) Gene Expression and Hematoendothelial Lineages", J. Biol. Chem., 290(40), (2015), 28107-28119.
Liu, Yunying, et al., "Generation of functional organs from stem cells", Cell Regeneration, 2:1, (2013), 1-6.
Nagashima, Hiroshi, et al., "Growing human organs in pigs—A dream or reality?", Theriogenology, 86(1), (2016), 422-426.
Rasmussen, Tara L., et al., "Etv2 rescues Flk1 mutant embryoid bodies", Genesis, 51(7), (2013), 471-480.
Wang, Xianlong, et al., "Efficient CRISPR/Cas9-mediated bialieiic gene disruption and site-specific knockin after rapid selection of highly active sgRNAs in pigs", Scientific Reports, 5: 13348, (2015), 1-11.
Wu, Jun, et al., "Interspecies Chimerism with Mammalian Pluripotent Stem Cells", Cell, 168(3), (2017), 473-486 (30 pgs.).
"U.S. Appl. No. 15/739,042, Restriction Requirement dated Jan. 8, 2020", 10 pgs.
"U.S. Appl. No. 15/739,066, Restriction Requirement dated Dec. 31, 2019", 10 pgs.
"Egyptian Application Serial No. PCT 1471/2017, Office Action dated Aug. 22, 2019", (w/ English Summary), 4 pgs.
"European Application Serial No. 16759528.9, Communication Pursuant to Article 94(3) EPC dated Nov. 22, 2019", 6 pgs.
"European Application Serial No. 16818785.4, Response filed Aug. 9, 2019 to Extended European Search Report dated Jan. 24, 2019", 6 pgs.
"Japan Approves First Human-Animal Embryo Experiments", Retrieved from the Internet: URL:<https://www.nature.com/articles/d41586-019-02275-3>; [retrieved on Nov. 19, 2019], (Jul. 26, 2019).

(56) References Cited

OTHER PUBLICATIONS

"Japanese Application Serial No. 2017-546061, Notification of Reasons for Refusal dated Jan. 15, 2020".
Rudnicki, Michael A., et al., "MyoD or Myf-5 is required for the formation of skeletal muscle", Cell 75(7), (1993), 1351-1359.
Zhou, et al., "Biochemical and Biophysical Research Communications", 375, (2008), 450-453.
"U.S. Appl. No. 15/739,042, Response filed Mar. 9, 2020 to Restriction Requirement dated Jan. 8, 2020", 11 pgs.
"U.S. Appl. No. 15/739,066, Response filed Feb. 28, 2020 to Restriction Requirement dated Dec. 31, 2019", 11 pgs.
"Canadian Application Serial No. 2,978,457, Voluntary Amendment filed Oct. 19, 2018", 10 pgs.
"European Application Serial No. 16759528.9, Response filed Jun. 5, 2019 to Communication dated Apr. 8, 2019 and to the Supplemental European Search Report", 11 pgs.
"Japanese Application Serial No. 2017-546061, Notification of Reasons for Refusal dated Jan. 15, 2020", (w/ English Translation), 12 pgs.
"New Zealand Patent Application Serial No. 735956, Voluntary Amendment filed Oct. 31, 2017", 45 pgs.
Lillico, Simon G., et al., "Live pigs produced from genome edited zygotes", *Scientific Reports*, 3: 2847, (2013), 1-4.
Zhou, Bin, et al., "Nkx2-5- and Isl1-expressing cardiac progenitors contribute to proepicardium", *Biochemical and Biophysical Research Communications*, 375(3), (2008), 450-453.
Zhou, Xiaoqing, et al., "Generation of CRISPR/Cas9-mediated gene-targeted pigs via somatic cell nuclear transfer", *Cell. Mol. Life Sci.*, 72, (2015), 1175-1184.
U.S. Appl. No. 16/952,807, filed Nov. 19, 2020, Humanized Skeletal Muscle.
U.S. Appl. No. 17/118,981, filed Dec. 11, 2020, Humanized Heart Muscle.
"U.S. Appl. No. 15/739,042, Non-Final Office Action dated Apr. 1, 2020", 27 pgs.
"U.S. Appl. No. 15/739,042, Response filed Jun. 12, 2020 to Non-Final Office Action dated Apr. 1, 2020", 12 pgs.
"U.S. Appl. No. 15/739,066, Non-Final Office Action dated Apr. 1, 2020", 24 pgs.
"U.S. Appl. No. 15/739,066, Response filed Jun. 30, 2020 to Non-Final Office Action dated Apr. 1, 2020", 11 pgs.
"U.S. Appl. No. 16/952,807, Preliminary Amendment filed Feb. 1, 2021", 7 pgs.
"U.S. Appl. No. 16/952,807, Preliminary Amendment filed Nov. 19, 2020", 8 pgs.
"U.S. Appl. No. 17/118,981, Preliminary Amendment filed Dec. 11, 2020", 9 pgs.
"Chinese Application Serial No. 201680024200.8, Response filed Dec. 29, 2020 to Office Action dated Jun. 15, 2020", (w/ English Translation of Claims), 25 pgs.
"Chinese Application Serial No. 201680049673.3, Office Action dated Jan. 5, 2021", (w/ Concise Statement of Relevance), 11 pgs.
"Chinese Application Serial No. 201680050242.9, Office Action dated Jan. 12, 2021", (w/ Concise Statement of Relevance), 9 pgs.
"European Application Serial No. 16759528.9, Response filed Mar. 20, 2020 to Communication Pursuant to Article 94(3) EPC dated Nov. 22, 2019", 25 pgs.
"European Application Serial No. 16818785.4, Response filed Feb. 5, 2021 to Communication Pursuant to Article 94(3) EPC dated Aug. 20, 2020", 11 pgs.
"European Application Serial No. 16818799.5, Communication Pursuant to Article 94(3) EPC dated Jun. 12, 2020", 5 pgs.
"European Application Serial No. 16818799.5, Response filed Dec. 11, 2020 to Communication Pursuant to Article 94(3) EPC dated Jun. 12, 2020", 6 pgs.
"Japanese Application Serial No. 2017-568252, Notification of Reasons for Rejection dated Jun. 29, 2020", (w/ English Translation), 12 pgs.
"Japanese Application Serial No. 2017-568279, Notification of Reasons for Rejection dated Apr. 6, 2020", (w/ English Translation), 8 pgs.
Cui, Chenchen, et al., "Gene targeting by TALEN-induced homologous recombination in goats directs production of β-lactoglobulin-free, high-human lactoferrin milk", Scientific Reports 5:10482. DIO: 10.1038/srep10482, (May 2015), 1-11.
Ifkovits, Jamie L., et al., "Inhibition of TGFβ Signaling Increases Direct Conversion of Fibroblasts to Induced Cardiomyocytes", PLoSONE, 9(2): e89678, (Feb. 2014), 1-11.
Kassar-Duchossoy, L., et al., "Mrf4 Determines Skeletal Muscle Identity in Myf5:Myod Double-Mutant Mice", Nature, 431, (2004), 466-471.
Matsunari, Hitomi, et al., "Blastocyst complementation generates exogenic pancreas in vivo in apancreatic cloned pigs", Proc. Natl. Acad. Sci. USA, 110(12), (May 30, 2018), 4557-4562.
McKarney, L. A., et al., "Myogenesis in Cultures of Uniparental Mouse Embryonic Stem Cells: Differing Patterns of Expression of Myogenic Regulatory Factors", Int. J. Dev. Biol., 41, (1997), 485-490.
Ott, M.-O., et al., "Early Expression of the Myogenic Regulatory Gene, myf-5, in Precursor Cells of Skeletal Muscle in the Mouse Embryo", Development, 111(4), (1991), 1097-1107.
Valdez, M. Renee, et al., "Failure of Myf5 to Support Myogenic Differentiation without Myogenin, MyoD, and MRF4", Developmental Biology, 219(2), (2000), 287-298.
Wu, Haibo, et al., "TALE nickase-mediated SP110 knockin endows cattle with increased resistance to tuberculosis", Proc. Natl. Acad. Sci. USA, https://www.pnas.org/content/112/13/E1530, (Mar. 2015), E1530-E1539.
Wu, Hongxia, et al., "Transcriptional regulation of vertebrate heart morphological development", (w/ English Abstract), Life Science Research, vol. 6, No. 4 (Suppl.), (Dec. 2002), 101-105.
Yao, Jing, et al., "Efficient bi-allelic gene knockout and site-specific knock-in mediated by TALENs in pigs", Scientific Reports 4:6926, DIO:10.1038/srep06926, (2014), 1-8.
Zhou, Lei, et al., "Cardiac Gene Activation Analysis in Mammalian Non-Myoblasic Cells by Nkx2-5, Tbx5, Gata4 and Myocd", PLOS ONE 7(6): e48028-e48028, (Oct. 2012), 1-12.
"U.S. Appl. No. 17/118,981, Supplemental Preliminary Amendment filed Feb. 22, 2021".
"Canadian Application Serial No. 2,978,457, Commissioner's Notice—Request for Examination Not Made mailed Mar. 24, 2021", 1 pg.
"Canadian Application Serial No. 2,991,053, Commissioner's Notice mailed Jul. 21, 2021", 1 pg.
"Canadian Application Serial No. 2,991,056, Commissioner's Notice mailed Jul. 21, 2121", 1 pg.
"Chinese Application Serial No. 201680024200.8, Office Action dated Jul. 16, 2021", (w/ English Translation), 10 pgs.
"Chinese Application Serial No. 201680049673.3, Office Action dated Sep. 6, 2021", (w/ English Translation), 10 pgs.
"Chinese Application Serial No. 201680049673.3, Response filed May 20, 2021 to Office Action dated Jan. 5, 2021", (w/ English Translation), 23 pgs.
"Chinese Application Serial No. 201680050242.9, Office Action dated Jul. 30, 2021", (w/ English Translation), 15 pgs.
"Chinese Application Serial No. 201680050242.9, Response filed May 12, 2021 to Office Action dated Jan. 12, 2021", (w/ English Translation), 18 pgs.
"European Application Serial No. 16759528.9, Summons to Attend Oral Proceedings mailed Mar. 12, 2021", 9 pgs.
"Korean Application Serial No. 10-2017-7027376, Voluntary Amendment Filed Feb. 16, 2021", (w/ English Translation of Claims), 11 pgs.
Hashimoto, Haruo, et al., "Development of Blastocyst Complementation Technology Without Contributions to Gametes and the Brain", *Experimental Animals*, vol. 68, No. 3, Retrieved from the Internet: <URL:https://www.ncbi.nlm.nih.gov/pmc/articles/PMC6699975/pdf/expanim-68-361.pdf>, (Jan. 1, 2019), 361-370.
"Chinese Application Serial No. 201680024200.8, Decision of Rejection dated Dec. 23, 2021", (w/ English Translation), 8 pgs.

(56) References Cited

OTHER PUBLICATIONS

"Chinese Application Serial No. 201680024200.8, Response filed Nov. 30, 2021 to Office Action dated Jul. 16, 2021", (w/ English Translation of Claims), 13 pgs.

"Chinese Application Serial No. 201680049673.3, Decision of Rejection dated Feb. 22, 2022", (w/ English Translation), 12 pgs.

"Chinese Application Serial No. 201680049673.3, Response filed Jan. 4, 2022 to Office Action dated Sep. 6, 2021", (w/ English Translation of Claims), 15 pgs.

"Chinese Application Serial No. 201680050242.9, Decision of Rejection dated Jan. 24, 2022", (w/ English Translation), 11 pgs.

"Chinese Application Serial No. 201680050242.9, Response filed Dec. 14, 2021 to Office Action dated Jul. 30, 2021", (w/ English Translation of Claims), 6 pgs.

"European Application Serial No. 16759528.9, EPO Written Decision to Refuse dated Feb. 11, 2022", 22 pgs.

"European Application Serial No. 16759528.9, Grounds of Appeal filed Jun. 13, 2022", 9 pgs.

"European Application Serial No. 16759528.9, Notice of Appeal filed Apr. 7, 2022 to EPO Written Decision to Refuse dated Feb. 11, 2022", 1 pg.

"European Application Serial No. 16759528.9, Response filed Nov. 5, 2021 to Summons to Attend Oral Proceedings mailed Mar. 12, 2021", 46 pgs.

"European Application Serial No. 16818799.5, Communication Pursuant to Article 94(3) EPC dated Apr. 13, 2022", 5 pgs.

"European Application Serial No. 16818799.5, Response filed Sep. 29, 2022 to Communication Pursuant to Article 94(3) EPC dated Apr. 13, 2022", 10 pgs.

"Mexican Application Serial No. MX/a/2017/011345, Office Action dated Sep. 3, 2021", (w/ English Translation), 10 pgs.

Das, S., et al., "Generation of human endothelium in pig embryos deficient in ETV2", (w/ Supplementary Information), Nature Biotechnology, 38(3), (2020), 31 pgs.

\* cited by examiner

| GENOTYPE | WT | HET | MUTANT |
|---|---|---|---|
| Ery-P | 14 ± 5 | 11 ± 5 | 0 |
| BFU-E | 23 ± 8 | 27 ± 5 | 0 |
| CFU-GM | 9 ± 9 | 11 ± 6 | 0 |
| CFU-G | 3 ± 3 | 3 ± 2 | 0 |
| CFU-M | 18 ± 10 | 28 ± 19 | 0 |
| CFU-GEMM | 63 ± 27 | 55 ± 19 | 0 |
| TOTAL | 116 ± 39 | 123 ± 39 | 0 |

FIG. 1B

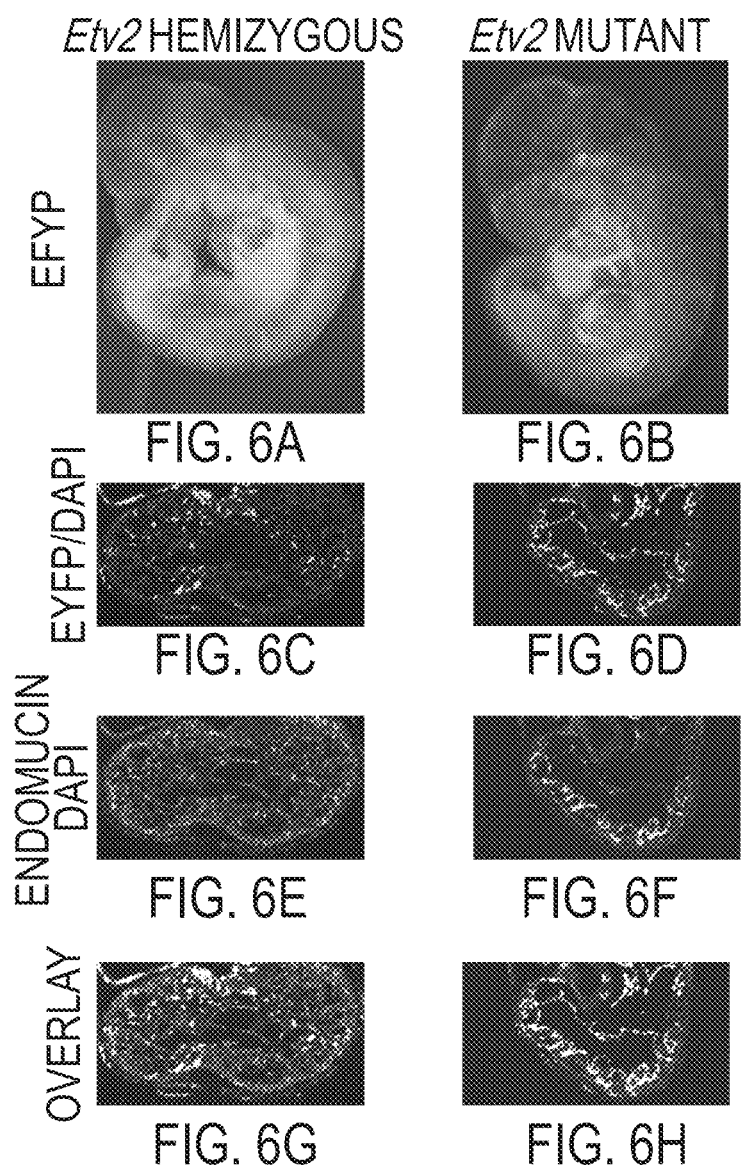

SEQUENCE LISTING

```
<160> NUMBER OF SEQ ID NOS: 21

<210> SEQ ID NO 1
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 1
ctggccggaa atcccc                                                      16

<210> SEQ ID NO 2
<211> LENGTH: 15
<212> TYPE: DNA
<213> ORGANISM: Artificial Sequence
<220> FEATURE:
<223> OTHER INFORMATION: A synthetic oligonucleotide

<400> SEQUENCE: 2
gggctgcacc aggct                                                       15

<210> SEQ ID NO 3
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 3
gatcccaagt cacacc                                                      16

<210> SEQ ID NO 4
<211> LENGTH: 15
<212> TYPE: DNA
<213> ORGANISM: Artificial Sequence
<220> FEATURE:
<223> OTHER INFORMATION: A synthetic oligonucleotide

<400> SEQUENCE: 4
cccctaaggg tcctg                                                       15

<210> SEQ ID NO 5
<211> LENGTH: 90
<212> TYPE: DNA
<213> ORGANISM: Artificial Sequence
<220> FEATURE:
<223> OTHER INFORMATION: A synthetic oligonucleotide
```

```
<400> SEQUENCE: 5
cgtctgctga ccaggggtct ggccggaaat ccccctcct gtggatccaa cagacacagg      60
acccttaggg gacctactgt gtgttcactg                                     90

<210> SEQ ID NO 6
<211> LENGTH: 524
<212> TYPE: DNA
<213> ORGANISM: Artificial Sequence
<220> FEATURE:
<223> OTHER INFORMATION: A synthetic oligonucleotide

<400> SEQUENCE: 6
tgaagcagcc ccagaacttc ctcctcaaag ccctcgaagg ggaaaacagc ctggtggaag     60
atcccaggtc gaccaaccaa cccccaccat atccccgca ggccccctgc ggattgtgac    120
gtctgctgac caggggtctg gccggaaatc cccttcctg tggatccaac agacacagga    180
cccttagggg acctactgtg tgttcactgt gtggtgggcc atgcagagga atcaaattca    240
gtagccactg gcctgcctgc tttgtgcctg ccctgtactg ggacttgtac atgaaacaga    300
cacaatcaat aactttcgaa tttacccact gtgtccccct ttgagaggac tcaagattcc    360
aaagagggct tactgtgtac cctccctgtg ccggggccat cagcgaatta gacctggtgc    420 ttgcccccc agtcacctat tctgttttcc tacttcaagc taagggccat agaacttaga    480
tcccaaggaa agtctaccct gttctgggaa caactgagcg ctta                     524

<210> SEQ ID NO 7
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 7
tgaagcagcc ccagaacttc                                                 20

<210> SEQ ID NO 8
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 8
tggcctccag tgtccttttc                                                 20

<210> SEQ ID NO 9
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 9
tagcctatcc cgaccgcat                                                  19

<210> SEQ ID NO 10
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 10
```

```
taagcgctca gttgttccca                                           20

<210> SEQ ID NO 11
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 11
tcatccttat ctgtcc                                               16

<210> SEQ ID NO 12
<211> LENGTH: 15
<212> TYPE: DNA
<213> ORGANISM: Artificial Sequence
<220> FEATURE:
<223> OTHER INFORMATION: A synthetic oligonucleotide

<400> SEQUENCE: 12
gcggagaccc agtcc                                                15

<210> SEQ ID NO 13
<211> LENGTH: 15
<212> TYPE: DNA
<213> ORGANISM: Artificial Sequence
<220> FEATURE:
<223> OTHER INFORMATION: A synthetic oligonucleotide

<400> SEQUENCE: 13
taccgaaccc agaag                                                15

<210> SEQ ID NO 14
<211> LENGTH: 17
<212> TYPE: DNA
<213> ORGANISM: Artificial Sequence
<220> FEATURE:
<223> OTHER INFORMATION: A synthetic oligonucleotide

<400> SEQUENCE: 14
actgtgggag acactca                                              17

<210> SEQ ID NO 15
<211> LENGTH: 90
<212> TYPE: DNA
<213> ORGANISM: Artificial Sequence
<220> FEATURE:
<223> OTHER INFORMATION: A synthetic oligonucleotide

<400> SEQUENCE: 15
cctccctaaa ctcagcttca tccttatctg tcccagggat tctaagcttc acagccggac   60
tgggtctccg cattaccgaa cccagaagct                                   90

<210> SEQ ID NO 16
<211> LENGTH: 83
<212> TYPE: DNA
<213> ORGANISM: Artificial Sequence
<220> FEATURE:
<223> OTHER INFORMATION: A synthetic oligonucleotide

<400> SEQUENCE: 16
cggactgggt ctccgcatta ccgaacccag aagctccatg gggcgcgggt gagtgtctcc   60
cacagtaact ggaggtttcg att                                         83
```

<210> SEQ ID NO 17
<211> LENGTH: 90
<212> TYPE: DNA
<213> ORGANISM: Artificial Sequence
<220> FEATURE:
<223> OTHER INFORMATION: A synthetic oligonucleotide

<400> SEQUENCE: 17
cggactgggt ctccgcatta ccgaacccag aagctccatg gtaagcttgg cgcgggtgag    60
tgtctcccac agtaactgga ggtttcgatt                                     90

<210> SEQ ID NO 18
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 18
cacaactctc gtcccgaaca                                                20

<210> SEQ ID NO 19
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 19
gaacggaccc caagtgagag                                                20

<210> SEQ ID NO 20
<211> LENGTH: 1661
<212> TYPE: DNA
<213> ORGANISM: Sus scrofa

<400> SEQUENCE: 20
tgagtcattg gaaacaaata cagacatcat aacacttcac tcctaaatac ctgtttcata    60
accttataaa gatagcttcc atatcataat accattatca catctaagaa atgactaat   120 tatctcatat tcagttcata ctctaatttc ctcatgtgcc taaactatga cagcatggaa   180
gggcatgatg gattctggag atgaagaaaa gtaggaggaa acgcacctca atttcccctt   240
tcataaagtc agggtaagac tagtacccac ttcctaagag aattaaacaa aggcccatgg   300
cacagttagt agcaagcaat gagccctcaa gaaatgttaa ccattattgt cactgttgtt   360
attgtttata ttgttgatgt tactgtctgc tgaagcagcc ccagaacttc ctcctcaaag   420
ccctcgaagg ggaaaacagc ctggtggaag atcccaggtc gaccaaccaa cccccaccat   480
atcccccgca ggcccctgc ggattgtgac gtctgctgac caggggtctg gccggaaatc   540 cccttcctg ttgcagataa gcctggtgca gcccagctga ccccaggccc tcctccccca   600
tcacctccct tgtcacagga tcaagtcccc aagccccctt ccctcccca ttccagtcaa   660 cccagaaaca cccctctgca ccccaggtca tgcccatccc attgtttccc aggctcctgc   720
tcaagtccaa gacaccccaa agctaccgtg gaggcttgag gccatcccag ggggcagagg   780
tgggtgggga gggggtggca cagcttggcc ccgcctcggc ccctgcaact tgacccgggc   840 tgcgacccc gctctgacgt cttggaaaat tccccctgc caggccccc agaggagggg    900 gtatgtggta tgaaatgggg ctgagacccc tggctggggg cacagggatc tgccagagaa   960
cattcactac tggcatccat ggacttgtgg aactgggatg aagcatcgcc acaggaagtg  1020

```
cccctgggga acagactgtc agggctggaa ggagctgaat tcgacttcta tttccctgaa   1080
ctggcactcc caggggacag gctgacagcg gagacatact ggaaaactgg ctcttcatcc   1140
ttatctgtcc cagggattcc acagccggac tgggtctccg cattaccgaa cccagaagct   1200
ccatggggcg cggaacccgt ccctcaggct cttccgtggt ccggagattg acagacctg    1260 ccgtacagcg gctcggtccc ttggagccgg gtctcccagg ccctggggtc tggctgccta   1320
gatttccaag gtcccattca gctgtggcag ttcctcctgg agctgctcca cgacgggacg   1380
cgtagcagct gcatccgctg acgggcaac agccgcgagt ccaactgtg cgaccccaaa     1440 gaggtggcgc ggctgtgggg cgaacgcaag aggaagcccg gcatgaatta tgagaagctg   1500
agccgaggcc tgcgttacta ctaccgccgc gacatcgtgc tcaagagcgg ggggcgcaag   1560
tacacgtacc gcttcggagg ccgagtgcca ggcctagcct atcccgaccg catgggggac   1620
ggacagggag cagcgaccca ataaaaatat ctggtcaagc c                       1661
```

<210> SEQ ID NO 21
<211> LENGTH: 221
<212> TYPE: PRT
<213> ORGANISM: Sus scrofa

<400> SEQUENCE: 21

```
Met Asp Leu Trp Asn Trp Asp Glu Ala Ser Pro Gln Glu Val Pro Leu
1               5                   10                  15

Gly Asn Arg Leu Ser Gly Leu Glu Gly Ala Glu Phe Asp Phe Tyr Phe
            20                  25                  30

Pro Glu Leu Ala Leu Pro Gly Asp Arg Leu Thr Ala Glu Thr Tyr Trp
        35                  40                  45

Lys Thr Gly Ser Ser Ser Leu Ser Val Pro Gly Ile Pro Gln Pro Asp
    50                  55                  60

Trp Val Ser Ala Leu Pro Asn Pro Glu Ala Pro Trp Gly Ala Glu Pro
65                  70                  75                  80

Val Pro Gln Ala Leu Pro Trp Ser Gly Asp Trp Thr Asp Leu Pro Tyr
                85                  90                  95

Ser Gly Ser Val Pro Trp Ser Arg Val Ser Gln Ala Leu Gly Ser Gly
            100                 105                 110

Cys Leu Asp Phe Gln Gly Pro Ile Gln Leu Trp Gln Phe Leu Leu Glu
        115                 120                 125

Leu Leu His Asp Gly Thr Arg Ser Ser Cys Ile Arg Trp Thr Gly Asn
130                 135                 140

Ser Arg Glu Phe Gln Leu Cys Asp Pro Lys Glu Val Ala Arg Leu Trp
145                 150                 155                 160

Gly Glu Arg Lys Arg Lys Pro Gly Met Asn Tyr Glu Lys Leu Ser Arg
                165                 170                 175

Gly Leu Arg Tyr Tyr Tyr Arg Arg Asp Ile Val Leu Lys Ser Gly Gly
            180                 185                 190

Arg Lys Tyr Thr Tyr Arg Phe Gly Gly Arg Val Pro Gly Leu Ala Tyr
        195                 200                 205

Pro Asp Arg Met Gly Asp Gly Gln Gly Ala Ala Thr Gln
    210                 215                 220
```

GENETICALLY MODIFIED PIG CELLS WITH AN INACTIVATED ETV2 GENE

CLAIM OF PRIORITY

This application is a U.S. national stage application filed under 35 U.S.C. § 371 from International Application Serial No. PCT/US2016/020768, which was filed Mar. 3, 2016, and published as WO2016/141234 on Sep. 9, 2016, which claims the benefit of priority of U.S. Provisional Patent Application No. 62/127,330, filed on 3 Mar. 2015, the benefit of priority of which is claimed hereby, and which applications are incorporated by reference herein in their entirety.

STATEMENT OF U.S. GOVERNMENT SUPPORT

This invention was made with government support under HL100407 awarded by the National Institutes of Health. The government has certain rights in the invention.

SEQUENCE LISTING

This document incorporates by reference herein an electronic sequence listing text file, which is filed in electronic format via EFS-Web. The text file is named "1552048.txt." is 12,288 bytes, and was created on Mar. 1, 2016.

BACKGROUND OF THE INVENTION

Blood is a major organ of the human body. It is composed of cells and plasma. The cellular part comprises red blood cells, white blood cells, and platelets. The plasma component consists of water and dissolved compounds such as proteins, sugars or electrolytes among others.

The formation of the blood begins during gastrulation. The first hematopoietic lineages appear in the blood island of the yolk sac. The differentiation of hematopoietic precursor cells is regulated by genetic programs. It was recently shown that a key factor of this genetic program is the gene Ets variant gene 2 (Etv2) (Stem cells. 2012 August; 30(8): 1611-1623. doi:10.1002/stem 1131). Ablation of the Etv2 gene in the mouse resulted in the loss of hematopoietic and endothelial lineages in the yolk sac. Forced overexpression of the Etv2 gene in the Etv2-mutant restored the hematological and endothelial lineages. Genesis 2013 July: 51 (7):471-480. Doi: 10.1002/dvg.22396.

Blood disorders may affect the production of red blood cells (i.e. anemias), the proliferation of white blood cells (i.e. leukemias), or the clotting of platelets (i.e. coagulopathies). Donated blood is used to treat these various disorders. Red blood cells are used to treat patients with chronic anemias associated with sickle cell anemia, thalassemia, aplastic anemia, leukemia or cancer. Platelets are used to control bleeding in patients undergoing surgery. Currently, the only source of human blood is a human donor.

SUMMARY OF THE INVENTION

The present invention is based on the novel finding that deletion of the Etv2 gene in pigs leads to the ablation of the hematopoietic and endothelial lineages at an early step of the hematoendothelial development. The present invention generates a pig blastocyst deficient of the pig Etv2 gene (and therefore deficient in pig vasculature and blood). By injecting human stem cells, such as iPS cells positive for the Etv2 gene into the mutant pig (deficient in Etv2) blastocyst, the invention generates a pig that produces human or humanized blood and vasculature derived from the human, stem cells, such as iPS cells. Every year, more than 300,000 Americans have coronary artery bypass grafting and would benefit from the use of such engineered coronary blood vessels.

Described herein is the development of ETV2 knockout pigs or other animals, such as cow or goat, as hosts for production of personalized human/humanized blood and vasculature for clinical applications. The progenitor cells that generate blood also generate the endothelium which represents the inner lining of blood vessels. In the absence of the endothelium, there is no vasculature and the developing embryos are non-viable. In addition to serving as a novel source of human/humanized tissues for the treatment of cardiovascular and hematopoietic disease, the humanized pigs will also serve as a large animal model to study the regeneration of human lineages and/or response(s) to pharmacological agents. Etv2 was discovered as a target of traditional cardiovascular and hematoendothelial transcription factors and signaling cascades and it was demonstrated that Etv2 regulates the specification and differentiation of hematoendothelial lineages. In addition, it was noted that the Etv2 mutant mouse embryos were nonviable and lacked endothelial/vascular and hematopoietic lineages. Using gene editing technologies, it is further established that ETV2 mutant porcine embryos lack hematopoietic and endothelial lineages. Based on the results, Etv2 is a master regulator for the hematoendothelial lineages during development. Described herein is the engineering of a humanized genetically modified animal surrogate.

One embodiment provides a non-human animal cell or blastocyst wherein the genome carries a mutation in both alleles of the ETV2 gene such that the non-human animal cell or blastocyst lacks functional ETV2 protein. In one embodiment, the mutation is a deletion of the ETV2 gene. In another embodiment, the non-human animal cell or blastocyst is a porcine, bovine, equine or goat.

One embodiment provides a chimeric non-human animal or blastocyst expressing human ETV2 and lacking expression of said non-human animal ETV2. In one embodiment, the non-human animal expresses human blood cells selected from the group consisting of white blood cells, red blood cells, platelets or a combination thereof. In another embodiment, the chimeric non-human animal expresses human endothelium. In one embodiment, the non-human animal is a porcine, bovine, equine or goat.

One embodiment provides a method for producing a chimeric non-human animal expressing a human ETV2 gene comprising: a) generating an ETV2 null non-human animal cell, wherein both copies of the non-human ETV2 gene carry a mutation that prevents production of functional ETV2 (by itself or with other genes) protein in said non-human animal; b) creating an ETV2 null non-human blastocyst by somatic cell nuclear transfer comprising fusing a nucleus from said ETV2 null non-human animal cell of a) into an enucleated non-human oocyte and activating said oocyte to divide so as to form an ETV2 null non-human blastocyst; c) introducing human stem cells into the ETV2 null non-human blastocyst of b); and d) implanting said blastocyst from c) into a pseudopregnant surrogate non-human animal to generate a chimeric non-human animal expressing human ETV2.

Another embodiment provides a method of producing human and/or humanized blood cells or vessels in a non-human animal comprising: a) generating an ETV2 null non-human animal cell, wherein both alleles of the non-human ETV2 gene carry a mutation that prevents production of functional ETV2 protein; b) creating an ETV2 null non-human blastocyst or morula by somatic cell nuclear transfer comprising fusing a nucleus from said ETV2 null non-human animal cell of a) into an enucleated non-human oocyte and activating said oocyte to divide so as to form an ETV2 null non-human blastocyst; c) introducing human donor stem cells into the ETV2 null non-human blastocyst of b); and d) implanting said blastocyst or morula from c) into a pseudopregnant surrogate non-human animal so as to generate a non-human animal expressing human and/or humanized blood cells or vessels. In one embodiment, the blood cells are human-induced pluripotent or human umbilical cord blood stem cell-derived white blood cells, red blood cells, and/or platelets.

In one embodiment, the non-human animal is a porcine, bovine, equine or goat. In another embodiment, the human donor stem cell is a tissue specific stem cell, pluripotent stem cell, multipotent adult stem cell, induced pluripotent stem cell or umbilical cord blood stem cell (UCBSC). In one embodiment, the donor providing the stem cells is the recipient of the humanized tissue or organ produced. In another embodiment, the human induced pluripotent cell is formed from a fibroblast cell.

One embodiment provides for a non-human animal produced by the methods described herein. Another embodiment provides a progeny non-human animal produced from the mating of two non-human animals generated from the methods described herein, wherein said progeny non-human animal expresses human ETV2, wherein the genome of said progeny non-human carries a homozygous deletion of said non-human animal ETV2 gene. In one embodiment, the non-human animal is a porcine, bovine, equine or goat.

One embodiment provides a gene knockout pig cell or blastocyst wherein the genome comprises a deletion of the ETV2 gene such that the pig cell or blastocyst lacks functional ETV2 protein, wherein the pig cell or blastocyst is homozygous for the deletion. In one embodiment, the sequence of wild type pig (*Sus scrofa*) ETV2 (ets variant 2) is provided at ENSSSCG000000002906. In another embodiment, the predicted *sus scrofa* ets variant 2 (ETV2) mRNA and protein sequence are provided as follows:

```
                                                            (SEQ ID NO: 20)
   1 tgagtcattg gaaacaaata cagacatcat aacacttcac tcctaaatac ctgtttcata 61 accttataaa gatagcttcc atatcataat accattatca catctaagaa aatgactaat 121 tatctcatat tcagttcata ctctaatttc ctcatgtgcc taaactatga cagcatggaa 181 gggcatgatg gattctggag atgaagaaaa gtaggaggaa acgcacctca atttcccctt 241 tcataaagtc agggtaagac tagtacccac ttcctaagag aattaaacaa aggcccatgg 301 cacagttagt agcaagcaat gagccctcaa gaaatgttaa ccattattgt cactgttgtt 361 attgtttata ttgttgatgt tactgtctgc tgaagcagcc ccagaacttc ctcctcaaag 421 ccctcgaagg ggaaaacagc ctggtggaag atcccaggtc gaccaaccaa cccccaccat 481 atcccccgca ggcccctgc ggattgtgac gtctgctgac caggggtctg gccggaaatc 541 ccccttcctg ttgcagataa gcctggtgca gcccagctga ccccaggccc tcctccccca 601 tcacctccct tgtcacagga tcaagtcccc aagcccctt cccctcccca ttccagtcaa 661 cccagaaaca ccctctgca ccccaggtca tgcccatccc attgtttccc aggctcctgc 721 tcaagtccaa gacacccaa agctaccgtg gaggcttgag gccatcccag ggggcagagg 781 tgggtgggga ggggtggca cagcttggcc ccgcctcggc ccctgcaact tgacccgggc 841 tgcgaccccc gctctgacgt cttggaaaat tccccctgc ccaggccccc agaggagggg 901 gtatgtggta tgaaatgggg ctgagacccc tggctggggg cacagggatc tgccagagaa 961 cattcactac tggcatccat ggacttgtgg aactgggatg aagcatcgcc acaggaagtg 1021 ccctgggga acagactgtc agggctggaa ggagctgaat tcgacttcta tttccctgaa 1081 ctggcactcc caggggacag gctgacagcg gagacatact ggaaaactgg ctcttcatcc 1141 ttatctgtcc cagggattcc acagccggac tgggtctccg cattaccgaa cccagaagct 1201 ccatggggcg cggaacccgt ccctcaggct cttccgtggt ccggagattg gacagacctg 1261 ccgtacagcg gctcggtccc ttggagccgg gtctcccagg ccctgggtc tggctgccta 1321 gatttccaag gtccattca gctgtggcag ttcctcctgg agctgctcca cgacgggacg 1381 cgtagcagct gcatccgctg gacgggcaac agccgcgagt tccaactgtg cgaccccaaa 1441 gaggtggcgc ggctgtgggg cgaacgcaag aggaagcccg gcatgaatta tgagaagctg
```

```
1501 agccgaggcc tgcgttacta ctaccgccgc gacatcgtgc tcaagagcgg ggggcgcaag 1561 tacacgtacc gcttcggagg ccgagtgcca ggcctagcct atcccgaccg catgggggac 1621 ggacagggag cagcgaccca ataaaaatat ctggtcaagc c
```

(SEQ ID NO: 21)

MDLWNWDEASPQEVPLGNRLSGLEGAEFDFYFPELALPGDRLTA

ETYWKTGSSSLSVPGIPQPDWVSALPNPEAPWGAEPVPQALPWSGDWTDLPYSGSVPW

SRVSQALGSGCLDFQGPIQLWQFLLELLHDGTRSSCIRWTGNSREFQLCDPKEVARLW

GERKRKPGMNYEKLSRGLRYYYRRDIVLKSGGRKYTYRFGGRVPGLAYPDRMGDGQGA ATQ

One embodiment provides an ETV2 mutant pig (deficient in Etv2). In another embodiment, a chimeric ETV2 mutant pig expresses human or humanized blood cells selected from the group consisting of white blood cells, red blood cells, platelets or a combination thereof, as well as human or humanized endothelium.

One embodiment provides a method for producing an ETV2 mutant pig comprising: a) generating an ETV2 null pig cell; b) creating an ETV2 null pig blastocyst by somatic cell nuclear transfer (SCNT) comprising fusing a nucleus from said ETV2 null pig cell of a) into an enucleated pig oocyte and activating said oocyte to divide so as to form an ETV2 null pig blastocyst; c) introducing human stem cells into the pig ETV2 null blastocyst.

Another embodiment provides a method of producing human or humanized blood cells and human or humanized endothelium in pigs comprising: a) generating an ETV2 null pig cell; b) creating an ETV2 null pig blastocyst by somatic cell nuclear transfer (SCNT) comprising fusing a nucleus from said ETV2 null pig cell of a) into an enucleated pig oocyte and activating said oocyte to divide so as to form an ETV2 null pig blastocyst; c) introducing human stem cells into the pig ETV2 null blastocyst (blastocoel cavity) of b) and d) implanting said blastocyst from c) into a pseudopregnant/surrogate pig so as to generate a pig with human/humanized blood cells and human/humanized endothelium (human stem cells are added to the gene edited blastocyst). In one embodiment, the blood cells and endothelium are human-iPS- or human umbilical cord blood stem cell-derived white blood cells, red blood cells, platelets and/or endothelium.

It would be useful to make human or humanized tissues and organs personalized to each recipient's immune complex. As disclosed herein, it is possible to do so by using a large animal as a host editing its genome to knock out or debilitate genes responsible for the growth and/or differentiation of a target organ and inoculating that animal at a blastocyst or zygote stage with donor stem cells to complement the missing genetic information for the growth and development of the organ. The result is a chimeric animal in which the complemented tissue (human/humanized organ) matches the genotype and phenotype of the donor. Such organs may be made in a single generation and the stem cell may be taken or generated from the patient's own body. As disclosed herein, it is possible to do so by simultaneously editing multiple genes in a cell (see, for example, WO 2015/168125, which is incorporated herein by reference).

Multiple genes can be targeted for editing using targeted nucleases and homology directed repair (HDR) templates in vertebrate cells or embryos.

One embodiment provides a method to produce humanized tissues in a non-human host animal comprising: i) genetically editing one or more genes responsible for a desired tissue or organ's growth and/or development in a cell or embryo, of the host; ii) complementing the host's lost genetic information by injecting an effective amount of stem cells from a donor into the cell, embryo, zygote or blastocyst (e.g., human-porcine blastocyst) to create a chimeric animal; so as to produce humanized tissue or organ (to produce a chimeric animal through the use of cell (e.g., stem cell) complementation).

In one embodiment, the stem cell is a human induced pluripotent stem cell (iPS cell) or a human umbilical cord blood stem cell. In one embodiment, the human iPS cell was formed from a fibroblast cell or any adult or somatic cells (e.g., human cells). In one embodiment, the ETV2 null pig cell was created using gene editing with TALENS (Gene: ETV2 ENSSSCGC00000002906).

Further described are methods of producing chimeric swine and methods of producing tissue from chimeric swine of the present invention. One embodiment provides a progeny swine produced from the mating of two pigs generated from methods described herein, wherein said progeny swine expresses human ETV2, wherein the genome of said progeny swine comprises a homozygous deletion of the pig ETV2 gene.

BRIEF DESCRIPTION OF THE DRAWINGS

FIGS. 1A-D. Etv2 is a master regulator of the hematopoietic and the endothelial lineages. (A) Etv2 mutant and wild-type littermate embryos were collected at E8.5, sectioned, and analyzed by hematoxylin-eosin staining and immunohistochemistry using endomucin antibody (α-endomucin). At this stage, primary heart vein (PHV), dorsal aorta (DA), and endocardium (End) are formed in wild-type embryos, whereas Etv2 mutant mice lack these structures. Anti-endomucin staining identifies vessels (arrowheads) and endocardium (arrows), which are absent in the mutant embryo. (B) Methylcellulose colony forming assay using yolk sac cells from Etv2 wild-type (Wt), heterozygous (Het), and mutant embryos at E 8.5. Note that wild-type and heterozygous animals for Etv2 have similar colony forming activity, whereas Etv2 mutant yolk sac cells have none. (C) Stably transfected ES cells lines were engineered to express Etv2 in a doxycycline (Dox)-inducible fashion. ES cells were differentiated for 4 days and Etv2 was induced by addition of Dox. Flow cytometric analysis after 5 days of induction demonstrated significant increase of both hematopoietic (CD45$^+$) and endothelial (PECA$^+$ or Tie$^{2+}$) lineages upon Etv2 induction. (D) Colony forming activity of the EBs after induction of Etv2 from day 3 to day 6. Note the increased hematopoietic activity upon induction of Etv2. Open bars: no induction, filled bars: Dox induction.

FIGS. 6A-H. Complementation of Etv2 mutant mouse embryo with wild-type ES cells. Blastocysts obtained from crossing Etv2$^{−/+}$ and Etv2$^{dFl/+}$ mice were injected with 10-15 EYFP labeled wild-type ES cells. Embryos were harvested at E10.5 and genotyped. A, B: Whole-mount epifluorescence image of the embryos showing the distribution of the wild-type ES cell progeny. C-H: Sections through the heart (ventricles) of the embryos shown in A and B, respectively. Panels show EYFP (C, D), Endomucin (E, F) immunohistochemistry, and overlaid images (G, H). Scale bars: 1000 µm (A, B), and 100 µm (C-H).

DETAILED DESCRIPTION OF THE INVENTION

Figure 1A:
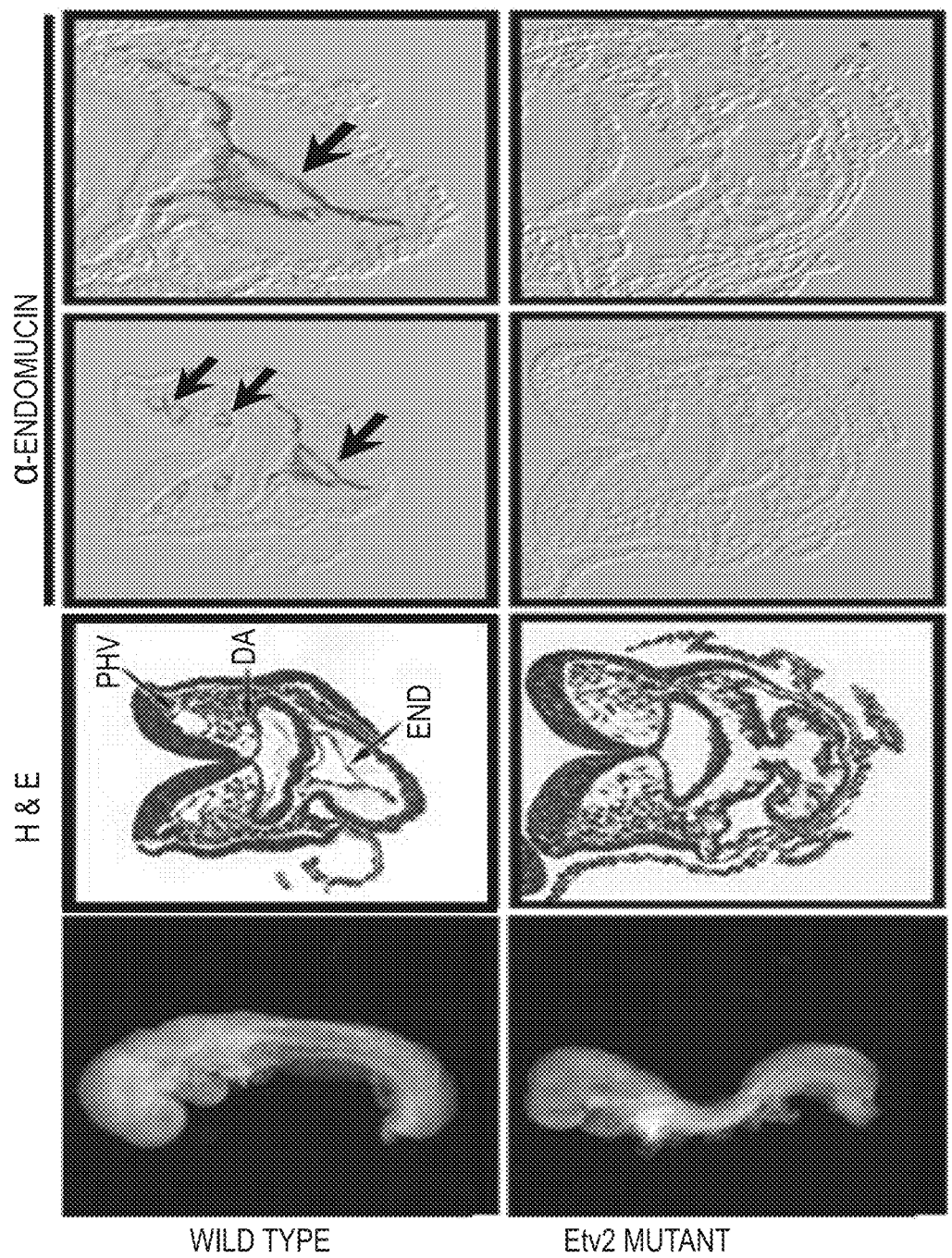

Described herein is the development of ETV2 (or ETV2 in combination with other gene knockouts) knockout animals, such as pigs, as hosts for production of personalized human/humanize blood and vasculature for clinical and preclinical applications. In addition to serving as a novel source of human/humanized tissues for the treatment of cardiovascular and hematopoietic disease, the humanized animals, such as pigs, will also serve as a large animal model to study the regeneration of human lineages or response(s) to pharmacological agents.

Blood and cardiovascular diseases are both common and deadly (1-3). These diseases are chronic, debilitating, and lethal and they warrant novel therapies. The blood and cardiovascular developmental programs have a number of overlapping features as both are lateral plate mesodermal derivatives and both are co-regulated by intersecting networks of transcription factors, signaling cascades and extracellular cues. Recent studies suggest that a common progenitor daughters the hematoendothelial lineages. Etv2/Etsrp71/ER71 is a target of traditional cardiovascular and hematoendothelial transcription factors and signaling cascades including: Mesp1, Flk1/Creb, and Nkx2-5. It has been demonstrated that Etv2 regulates the specification and differentiation of hematoendothelial lineages (4-17). In addition, Etv2 mutant mouse embryos were nonviable and had perturbed mesodermal (hematopoietic and endothelial) lineage development (9, 10). The data described herein support that ETV2 mutant porcine embryos are also nonviable and lack hematopoietic and endothelial lineages. Based on the results, Etv2 is a master regulator for the hematoendothelial lineages during development. Described herein are ETV2 knockout pigs as hosts for production of personalized human blood and vasculature for clinical applications. This humanized large animal model will be an important resource for regenerative medicine and will serve as a platform for generating personalized humanized porcine organs. This strategy has the capacity to have a profound impact on the development of emerging therapies for chronic cardiovascular and hematopoietic diseases and transplantation. In addition to serving as a novel source of human tissues for the treatment of cardiovascular and hematopoietic disease, the humanized pigs will also serve as a large animal model to study the regeneration of human lineages or response(s) to pharmacological agents.

Definitions

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Any methods and materials similar or equivalent to those described herein can be used in the practice or testing of the present invention. Specific and preferred values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The term "isolated" refers to a factor(s), cell or cells which are not associated with one or more factors, cells or one or more cellular components that are associated with the factor(s), cell or cells in vivo.

"Cells" include cells from, or the "subject" is, a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, or orangutan), rat, sheep, goat, cow and bird.

The terms "pig" and "swine" and "porcine" are used interchangeably are generic terms referring to the same type of animal without regards to gender, size or breed.

Transcription Activator-Like Effector Nucleases (TALENs) are artificial restriction enzymes generated by fusing the TAL effector DNA binding domain to a DNA cleavage domain. These reagents enable efficient, programmable, and specific DNA cleavage for genome editing in situ. Transcription activator-like effectors (TALEs) are proteins that bind DNA in a sequence specific way. By fusing such a TALE to a nuclease (e.g., FokI endonuclease) a highly specific DNA "scissor" is made (these molecules can be engineered to bind any DNA sequence). The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN, which references the handedness of DNA.

Once the TALEN genes have been assembled they are inserted into plasmids; the plasmids are then used to transfect the target cell where the gene products are expressed and enter the nucleus to access the genome. TALENs can be used to edit genomes by inducing double-strand breaks (DSB) and optionally inserting a cargo/preselected gene, which cells respond to with repair mechanisms. In this manner, they can be used to correct mutations in the genome which, for example, cause disease.

Genetic engineering, including gene editing, can be carried out by any method available to an art worker, for example, by the use of tartgeted endonucleases, and homology directed repair (HDR), TALEN, CRISPR (e.g., CAS9/CRISPR), recombinase fusion molecules, synthetic porcine artificial chromosomes, meganucleases, zinc finger or rAAV based systems for gene editing (e.g., to knockout desired target genes). Further, a variety of nucleic acids can be introduced into cells, for knockout purposes, for inactivation of a gene (such as interfering RNAs (shRNA, siRNA, dsRNA, RISC, miRNA) or express a gene.

Somatic cell nuclear transfer (SCNT) is a laboratory technique for creating a viable embryo from a body cell and an egg cell. The process of somatic cell nuclear transplant involves two different cells. The first being a female gamete, known as the ovum (egg/oocyte). The second being a somatic cell, referring to the cells of the human body. Skin cells, fat cells, and liver cells are only a few examples. The nucleus of the donor egg cell is removed and discarded, leaving it 'deprogrammed.' The nucleus of the somatic cell is also removed but is kept, the enucleated somatic cell is discarded. What is left is a lone somatic nucleus and an enucleated egg cell. These are then fused by squirting the somatic nucleus into the 'empty' ovum. After being inserted into the egg. the somatic cell nucleus is reprogrammed by its host egg cell. The ovum, now containing the somatic cell's nucleus, is stimulated with a shock and will begin to divide. The egg is now viable and capable of producing an adult organism containing all the necessary genetic information from just one parent. Development will ensue normally and after many mitotic divisions, this single cell forms a blastocyst (an early stage embryo with about 100 cells) with an identical genome to the original organism (i.e. a clone). Stem cells can then be obtained by the destruction of this clone embryo for use in therapeutic cloning or in the case of reproductive cloning the clone embryo is implanted into a host mother (pseudopregnant/surrogate) for further development and brought to term.

"Chimera" refers to is a single organism composed of genetically distinct cells.

"Humanized" refers to an organ or tissue harvested from a non-human animal whose protein sequences and genetic complement are more similar to those of a human than the non-human host.

"Organ" refers to a collection of tissues joined in a structural unit to serve a common function. "Tissue" as used herein refers to a collection of similar cells from the same origin that together carry out a specific function.

A nullizygous organism carries two mutant or missing alleles for the same gene. The mutant/missing alleles are both complete loss-of-function or 'null' alleles, so homozygous null and nullizygous are synonymous.

A gene knockout (abbreviation: KO) is a genetic technique in which both of an organism's alleles are made inoperative ("knocked out" of the organism). The term knockout, inactivated, and disrupted are used interchangeably herein to mean that the targeted site is changed so that the gene expression product is eliminated or greatly reduced. Also known as knockout organisms or simply knockouts. The term also refers to the process of creating such an organism, as in "knocking out" a gene. The technique is essentially the opposite of a gene knockin.

The term gene is broad and refers to chromosomal DNA that is expressed to make a functional product. Genes have alleles. Gene editing may be non-allelic or bi-allelic.

The terms "comprises," "comprising," and the like can have the meaning ascribed to them in U.S. Patent Law and can mean "includes," "including" and the like. As used herein, "including" or "includes" or the like means including, without limitation.

Exogenic Organ Production is Needed to Meet the Demand for Organ Transplants.

Currently, the only definitive therapy for advanced end stage organ failure is transplantation. The limiting factor for transplantation is donor organ availability. Hundreds of thousands of patients could benefit from such therapy, but are not suitable transplant candidates due to their comorbid diseases. Therefore, there is a significant shortage of cadaveric or living-related donor organs. Furthermore, transplantation of organs requires lifelong immunosuppression which also has deleterious side effects. Herein the generation of humanized tissues in pigs is described, which will serve as an unlimited source of organs for transplantation and provide a paradigm shifting platform for the treatment of cardiovascular and hematopoietic diseases.

Intense interest has focused on xenogenic transplantation. For example, a rat pancreas was produced in a mouse by the process of blastocyst complementation (27). In these studies, blastocysts mutant for Pdx1, the master regulatory gene for pancreatic development, were injected with pluripotent stem cells from wild-type (WI) rat (rPSCs) (27). Transfer of the rPSC-injected blastocysts into surrogate mouse dams gave rise to mouse chimeras with functional pancreata composed of rat cells. These studies emphasized the importance of generating blastocysts deficient for a key developmental regulatory factor, so that the embryo completely lacks the target organ. These mutant hosts then provide a developmental "niche", for the healthy donor stem cells to populate and generate a donor-derived organ. The blastocyst complementation strategy has also produced organs such as the kidney, thymus and liver in rodents, and recently the pancreas in pigs (28-31).

Using the gene-editing platform or any method available to an art worker, various developmental genes can be mutated to generate organ-deficient animals, such as pigs, upon which blastocyst complementation can be deployed for the generation of exogenic organs.

Etv2 (ENSSSCG00000002906) is a Master Regulatory Gene for Endothelial and Hematopoietic Lineages.

The Etv2 gene locus was mutated to generate endothelial and hematopoietic deficient pig embryos for several reasons. First, the inventors have demonstrated that Etv2 is a master regulatory gene for endothelial and hematopoietic development in mice (7-9). Using genetic lineage tracing strategies, it was demonstrated that Etv2 expressing cells give rise to endothelial and hematopoietic lineages (9, 10). Second, a global gene deletional strategy was undertaken and demonstrated that Etv2 mutant mouse embryos were nonviable as they lacked endothelial and hematopoietic lineages (FIG. 1A, B) (8). Using transcriptome analysis, it was determined that Tie2 was markedly dysregulated in the absence of Etv2 (7, 8). Moreover, using transgenic technologies and molecular biological techniques (transcriptional assays, EMSA, ChIP and mutagenesis), it was verified that Spi1, Tie2 and Lmo2 were direct downstream targets of Etv2 (7, 8, 1). Third, forced overexpression of Etv2 in the differentiating ES/EB system significantly increased the populations of endothelial and hematopoietic lineages, demonstrating that Etv2 is a single factor that has the capacity to govern molecular cascades that will induce both lineages (FIG. 1 C, D) (8).

Fourth, the functional role of Etv2 was defined in mesodermal lineage specification and the molecular pathways upstream of Etv2, as well as its downstream targets were defined. Microarray analysis of wild-type (Wt) and Etv2 mutant mice revealed that cardiac specific transcripts were overrepresented in Etv2 mutants, suggesting that Etv2 suppresses the differentiation of cardiac lineages (9). In support of this finding, overexpression of Etv2 suppressed cardiac differentiation in ES/EB cells while inducing the endothelial and hematopoietic programs. From these studies, a role for Etv2 was defined in the specification of the mesodermal lineages as a necessary and sufficient factor for endothelial and hematopoietic differentiation as well as an inhibitor of cardiac differentiation (FIG. 2) (9).

Figure 2:
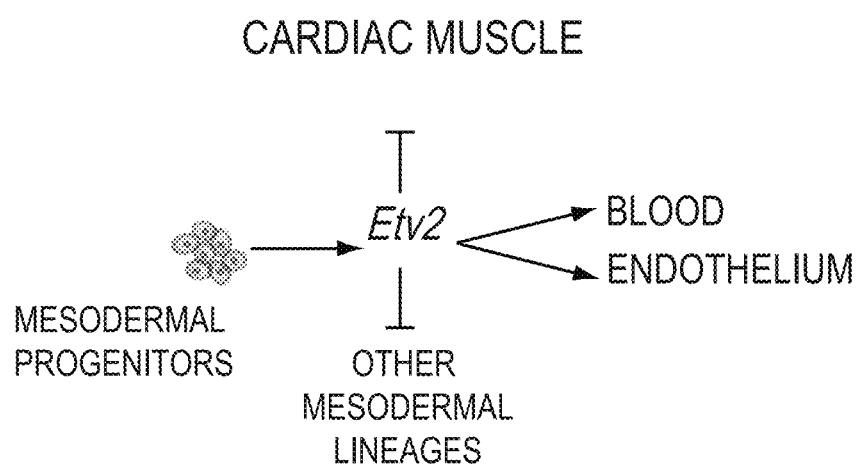
FIG. 2. Proposed role of Etv2 in specification of the mesodermal lineages.
Figure 3B:
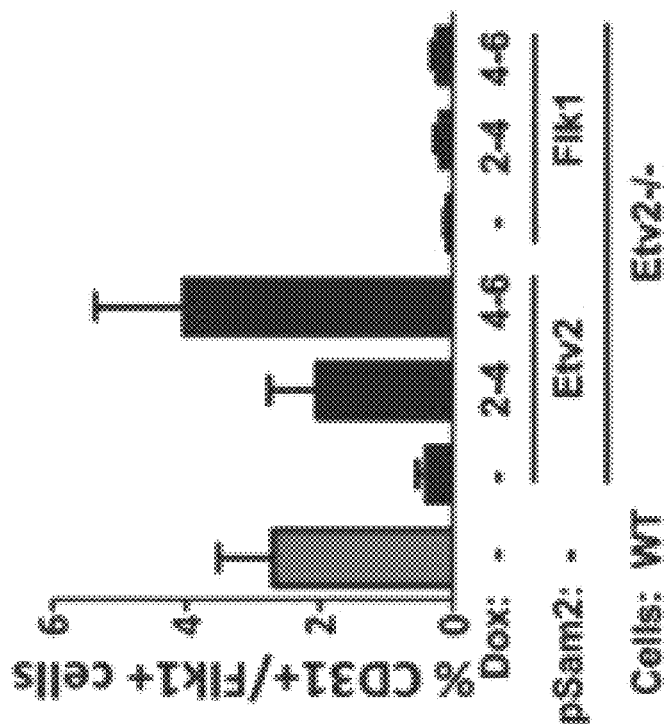
FIGS. 3A-G. Etv2 but not Flk1 can rescue the endothelial and hematopoietic phenotype of Etv2 mutant ESCs/EBs. Quantification of FACS analysis demonstrating that Etv2 and Flk1 can rescue the endothelial differentiation of Flk1−/− ESCs/EBs (A) but only Etv2 can rescue the Etv2−/− ESCs/EBs (B). The same results were obtained with hematopoietic markers (data not shown). The summary of the lineages and rescue studies for Etv2 and Flk1 are presented in panel (C). Gata2 physically interacts and amplifies Etv2 activity. (D) Schematic illustration of the Etv2-Gata2 construct. Etv2 and Gata2 are linked through the 2A peptide sequence and are equally expressed. The fusion construct was translated into two proteins, Etv2 and Gata2, through the ribosome skipping mechanism. (E-F) Co-expression of Etv2 and Gata2 in EBs results in enhanced hematopoietic and endothelial lineage differentiation. The EBs were treated with doxycycline (+Dox) or left untreated (−Dox) from EB day 3 to day 4 and harvested for FACS analysis on Day 6. The hematopoietic lineage is identified as the c-Kit$^+$/CD41$^+$ cell population (E), and the endothelial lineage is represented as Flk1$^+$/CD31$^+$ (F). Panel G highlights upstream regulators and downstream targets for Etv2 in endothelial and hematopoietic lineages.
Figure 3A:
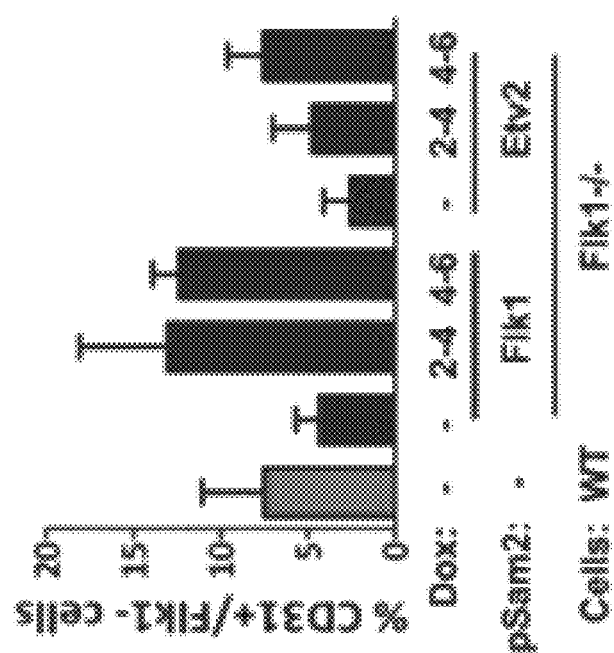
Figure 3C:
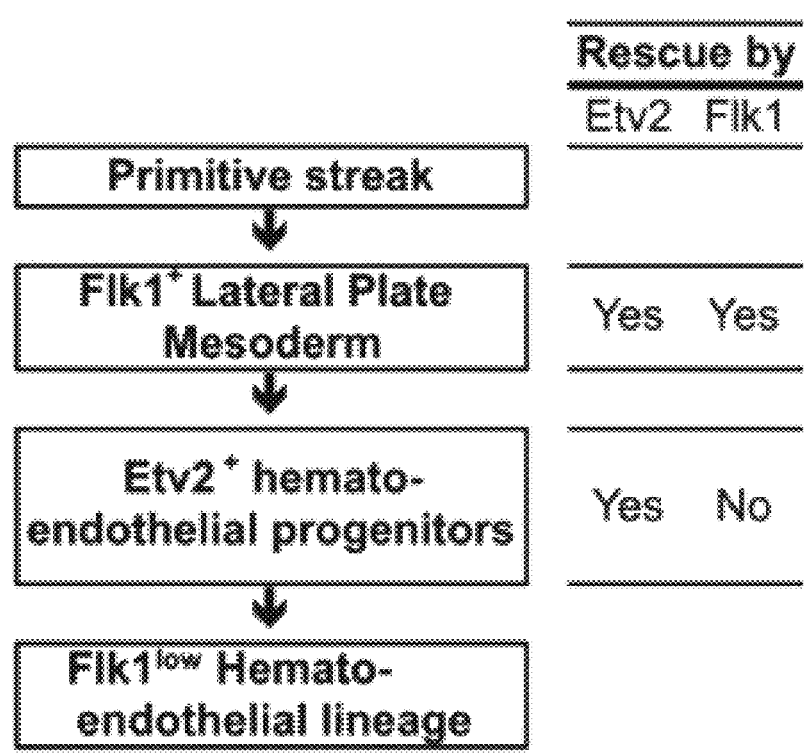
Figure 3D:
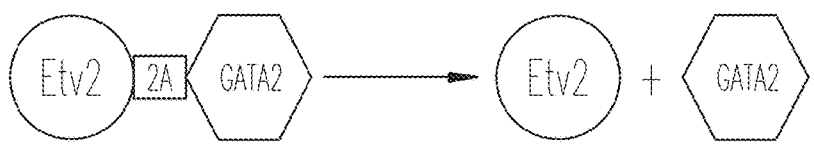
Figures 3E, 3F:
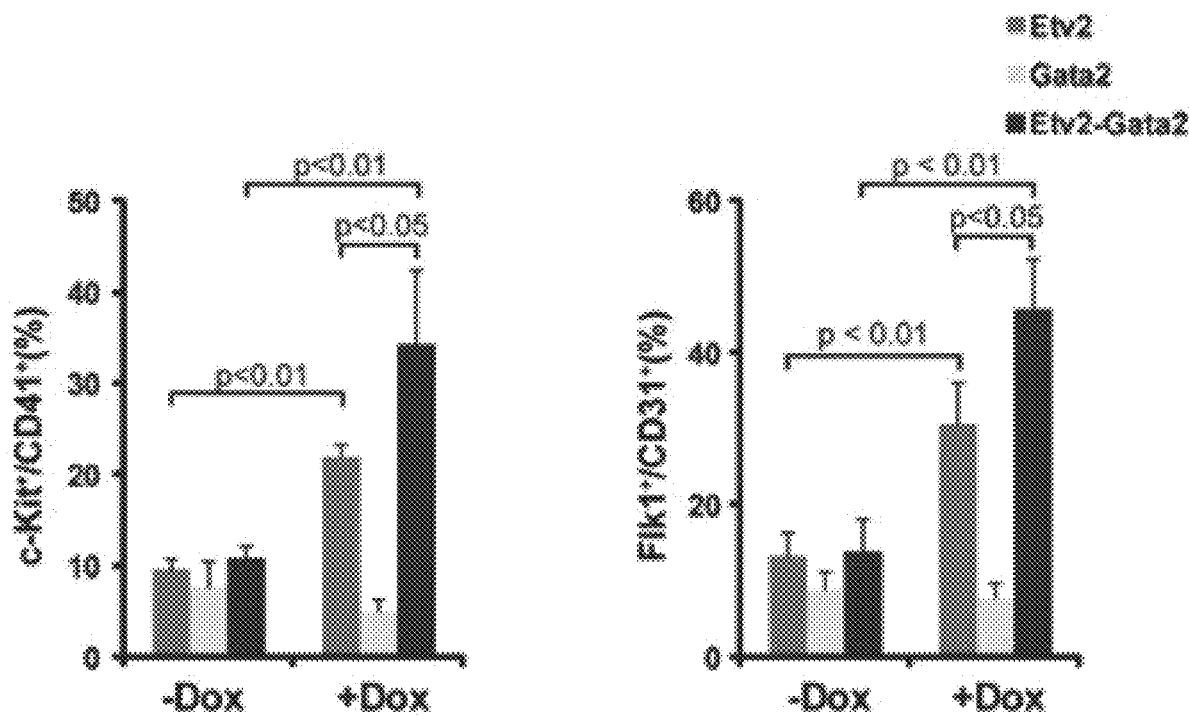
Figure 3G:
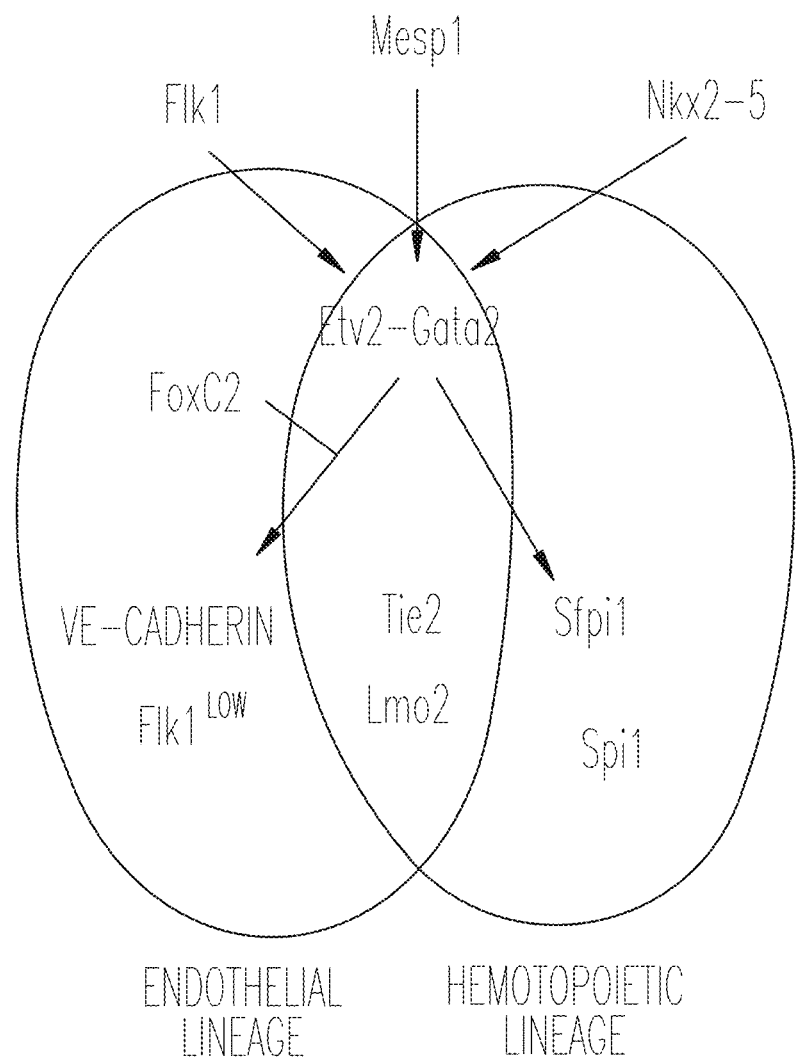

Several key findings regarding the molecular pathways involving Etv2 are summarized in FIG. 2. First, the genetic hierarchy of Flk1 and Etv2 was determined (12). Flk1 mutant and Etv2 mutant ES cells were utilized, both unable to generate hematopoietic and endothelial lineages, and tested whether those phenotypes can be rescued by overexpression of Etv2 or Flk1. The results demonstrated that the endothelial and hematopoietic potential of Flk1 mutant ESCs/EBs were rescued by both Etv2 and Flk1. but the Etv2 mutant phenotype was rescued only by Etv2 and not by Flk1. This finding indicates that (1) Etv2 is genetically downstream of Flk1 and that (2) the down-regulation of Etv2 is responsible for the Flk1 mutant phenotype. Therefore, the hierarchy of Flk1→Etv2 in the endothelial progenitors was established. Second. Gata2 was identified as a co-factor of Etv2 function (FIG. 3D-F) (11). By overexpressing Gata2 and Etv2 in ES cells at a 1:1 stoichiometry, it was demonstrated that both hematopoietic and endothelial differentiation were enhanced compared to Etv2 alone. Gata2 by itself did not enhance differentiation, suggesting that it acts as an amplifier of Etv2 function. Third, recent studies in mouse and zebrafish demonstrate that Etv2 regulates lineage restricted microRNAs that further govern the specification of endothelial and hematopoietic lineages (data not shown). In summary, upstream and downstream factors were defined, as well as co-factors that interact with Etv2 to promote the differentiation of hematopoietic and endothelial lineages (FIG. 3G).

These and other results support the rationale that Etv2 is a candidate for gene-editing in porcine models, as the studies predict that Etv2 mutant animals will completely lack the endothelial and hematopoietic lineages and provide a niche for human stem cells to populate. The compositions and methods described herein will yield a vascular system that will be lined or populated with human endothelial cells, making it an ideal tissue to transplant. Moreover, human blood will be produced in a porcine surrogate model.

The fifth reason that Etv2 is distinct from other genes emerges from studies of xenogenic transplantation. Although proof-of-principle studies of interspecific complementation and subsequent transplantation of exogenic organs have been successful, it was noted that vessels that serve those organs are host-derived (1, 2). These findings raise a significant concern, considering the well-known importance of vascular surfaces in organ rejection, specifically the hyperacute rejection of xenotransplanted pig tissues (13). In fact, humanization of the endothelial lineage is needed for the development of most exogenic organs. Etv2 is an ideal candidate for this purpose.

The humanized large animal model will be an important resource for regenerative medicine and will serve as a platform for making personalized organs. This strategy can transform the current clinical practice paradigms for chronic cardiovascular and hematopoietic diseases and transplantation. To date, exogenic transplantation of organs has been performed between mouse and rat (27, 29); and pig and pig (31), and no successful development of humanized organs in large animal models have been reported. Incorporated herein by reference is U.S. Provisional Application Ser. No. 62/247,092.

The following examples are intended to further illustrate certain particularly preferred embodiments of the invention and are not intended to limit the scope of the invention in any way.

EXAMPLES

Materials and Methods

Sow/gilts: Domestic maternal female pigs (8-12 months old) will be used as embryo transfer recipients and cared for and maintained as regular domestic pigs in prospective gestation and farrowing under approved IACUC protocols.

Estrus Synchronization and Insemination: Sows will be given 6.8 mL of Matrix (altrenogest 2.2 mg/mL) mixed into their morning feed on days 11-22 of their estrus cycle to synchronize estrus. Lutalyse (2 cc) will be administered IM on the last day of Matrix and four days later. Sows will be checked for estrus twice daily, starting day 6 after the end of Matrix administration. The sows will be inseminated with semen from selected boars up to three times after first detected in estrus. Sows will be checked for pregnancy between days 23-90 of gestation using either Doppler ultrasound or transabdominal ultrasound with a linear 5 mHz transducer. Neither form of ultrasound is invasive and does not harm the sow or fetuses. Blood samples may be taken from the pregnant gilts/sows to determine if any diseases are present at the request of the veterinarian or for genetic analysis.

Embryo Transfer: Reconstructed cloned embryos are surgically transferred into uteri of asynchronous recipient female pigs. For surgical embryo transfer, anesthesia is induced with a combination of the following: ketamine (2 mg/kg), tiletamine/zolazepam (0.25 mg/kg), xylazine (1 mg/kg), and atropine (0.03 mg/kg; all from Iowa Veterinary Supply) General anesthesia will be maintained for the rest of the procedure with isoflurane or sevoflurane (5% induction, maintenance at 1-4% to keep at surgical plane). While in dorsal recumbence, the recipients are aseptically prepared for surgery and a caudal ventral incision is made to expose and examine the reproductive tract, including the uterus, oviducts and ovaries. Typically, 150-200 reconstructed cloned embryos are placed in the isthmus of the oviduct using a 5.5-inch TomCat® catheter (Iowa Veterinary Supply). The uterus is placed back into the peritoneal cavity, and the recipient animals are sutured and placed into postoperative recovery. During gestation, real-time ultrasound examination is used to confirm and monitor pregnancy using an Aloka 500 Ultrasound Scanner (Aloka Co. Ltd, Wallingford, Conn.) with an attached 3.5 MHz transabdominal probe. Recipient husbandry will be maintained as normal gestating sows. For piglet production, recipients will be allowed to farrow naturally or will be delivered by c-section prior to day 118 of gestation. Colostrum feeding and intensive neonatal support, including Nurtinger rearing units, are available when necessary.

ETV2 Knockout Pig Embryos Lack Hematopoietic and Endothelial Lineages.

Figure 4A:
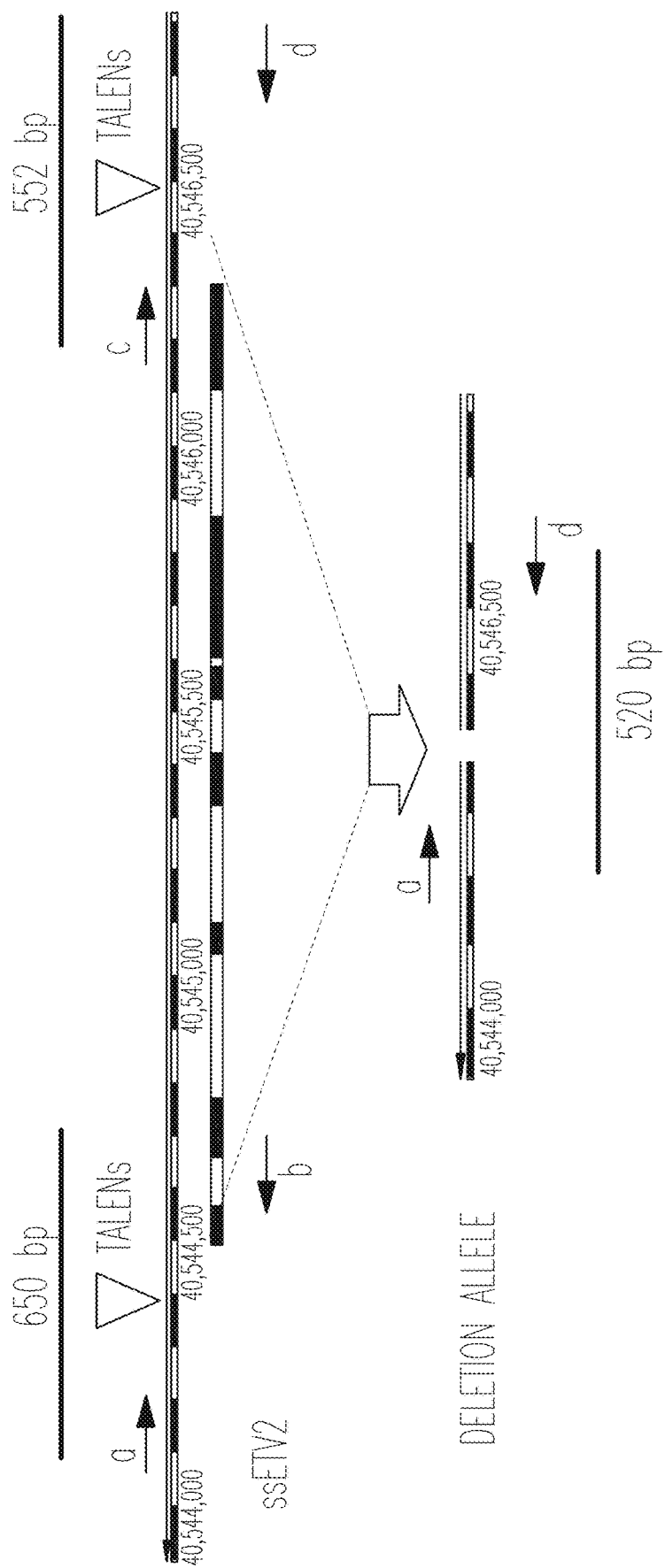
FIGS. 4A-B. TALEN-mediated knockout of ETV2. (A) Three-tiered PCR assay utilized to detect gene editing. Amplification from primers a-d indicated a deletion allele was present. To distinguish between heterozygous and homozygous clones, primers a-b and c-d were used to amplify the wild type allele. Only when the a-d product is present and both a-b, c-d products are absent is the clone considered homozygous for the deletion allele. (B) Clones fitting these criteria are enclosed by a green box.
Figure 4B:
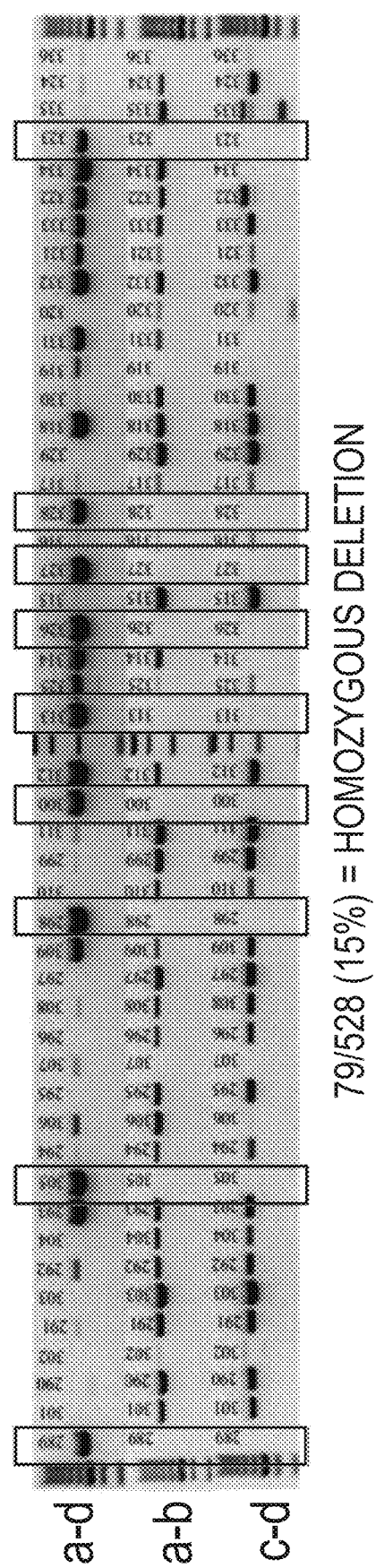
Figures 5A, 5B:
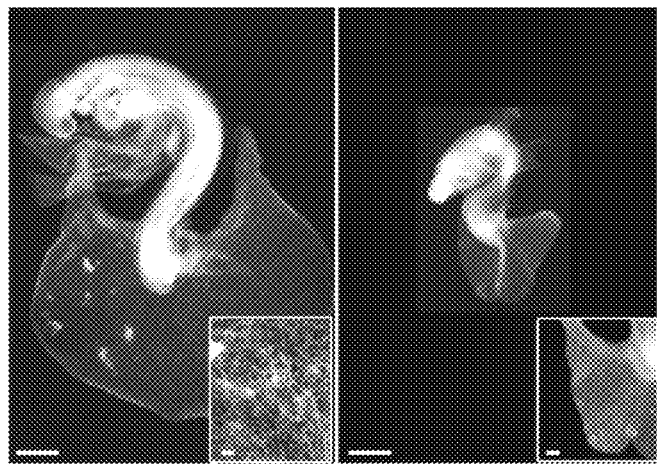
FIGS. 5A-H. Loss of porcine ETV2 recapitulated the mouse Etv2 mutant phenotype. Wild-type E18.0 pig embryo (A) and (B) ETV2 knockout embryo at the same developmental stage. Insets show enlarged views of the allantois. Note an abnormal overall morphology with lack of vascular plexus formation in the mutant (inset). (C-H) Sections through the allantois (C, D), the heart level (E, F) and the trunk level (G, H) of the embryos shown in A and B, respectively, were stained for Tie2, an endothelial marker; Gata4, a cardiac lineage marker: and 4′,6-diamidino-2-phenylindole (DAPI), a nuclear counterstain. The wild-type allantois was highly vascularized with Tie2 positive endothelial lining and contained blood (C, arrows), whereas, the mutant lacked these populations (D). The endocardium, cardinal veins (CV), and dorsal aortae (DA) are clearly visible in the wild-type embryo (E, G). In contrast, ETV2 null embryos completely lacked these structures although the heart progenitors and gut marked by Gata4 (green) were present (F and H, respectively). Scale bars: 1000 µm (A, B), 200 µm (insets in A, B), 100 µm (C-H).
Figures 5C, 5D:
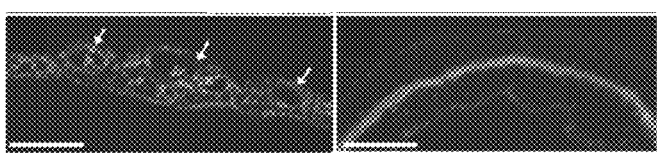
Figures 5E, 5F:
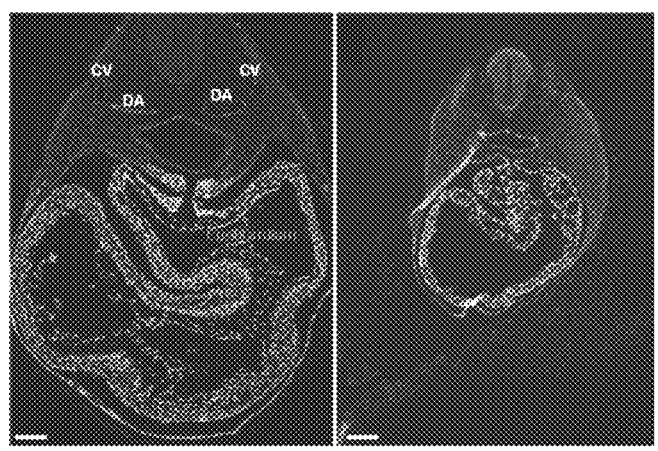
Figures 5G, 5H:
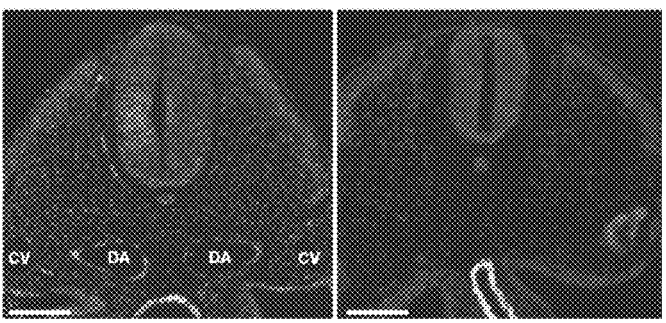

Previous studies have demonstrated that Etv2 plays a role in vasculogenesis and hematopoiesis in the mouse, as embryos lacking Etv2 are lethal at approximately E9.5 with an absence of vasculature and blood (7-10). To examine the role of ETV2 (ENSSSCG00000002906) in the pig, the entire ETV2 coding sequence was removed using two TALEN pairs flanking the gene in porcine fibroblasts (FIG. 4).

1) ETV2 Deletion Strategy

TALENs:

```
ETV2 5-2 (from 5' to 3')
Left:    CTGGCCGGAAATCCCC    (SEQ ID NO: 1)

Right:   GGGCTGCACCAGGCT     (SEQ ID NO: 2)

ETV2 3-2 (from 5' to 3')
Left:    GATCCCAAGTCACACC    (SEQ ID NO: 3)

Right:   CCCCTAAGGGTCCTG     (SEQ ID NO: 4)
```

2) HDR Stitching template: This template fuses the 5' and 3' TALEN induced breaks in a predictable manner. It also increased the efficiency of recovering the deletion allele.

HR Oligo

CGTCTGCTGACCAGGGGTCTGGCCG-GAAATCCCCCTTCCTGT
GGATCCaacagacacaggacccttaggggacctactgtgtgttcactg
(SEQ ID NO:5)

Underlinelowercase=42nt of homology from right side of ETV2 3.2 cut site

UPPER CASE BOLD=42nt of homology from left side of ETV2 5.2 cut site

UPPERCASEUNDERLINED=Inserted BamHI site

FullsequencefromETV25'NJF1toETV23'NJR1: This is the predicted PCR product when the deletion allele is uses the above template for repair/fusion.

(SEQ ID NO: 6)
tgaagcagccccagaacttcctcctcaaagccctcgaaggggaaaacagc ctggtggaagatcccaggtcgaccaaccaaccccaccatatccccgca ggcccctgcggattgtgaCGTCTGCTGACCAGGGGTCTGGCCGGAAATC

CCCCTTCCTGTGGATCCaacagacacaggacccttaggggacctactgtg tgttcactgtgtggtgggccatgcagaggaatcaaattcagtagccactg gcctgcctgctttgtgcctgccctgtactgggacttgtacatgaaacaga cacaatcaataactttcgaatttacccactgtgtccccctttgagaggac tcaagattccaaagagggcttactgtgtaccctccctgtgccggggccat cagcgaattagacctggtgcttgccccccagtcacctattctgttttcc tacttcaagctaagggccatagaacttagatcccaaggaaagtctaccct gttctgggaacaactgagcgctta 3) Screening Primers:

ssETV2 5' NJ F1: TGAAGCAGCCCCAGAACTTC (SEQ ID NO: 7)

ssETV2 5' N1 R1: TGGCCTCCAGTGTCCTTTTC (SEQ ID NO: 8)

ssETV2 3' NJ F1: TAGCCTATCCCGACCGCAT (SEQ ID NO: 9)

ssETV2 3' NJ R1: TAAGCGCTCAGTTGTTCCCA (SEQ ID NO: 10)

The process was 15% efficient at complete gene removal; 79/528 of the genotyped clones were homozygous for the deletion of the ETV2 gene. ETV2 homozygous knockout fibroblast clones were used for nuclear cloning (Somatic Cell Nuclear Transfer; SCNT) to generate ETV2 null embryos which were transferred to surrogate sows. The cloning efficiency was 29%.

Embryos were harvested and analyzed at E18.0 (FIG. 5). At E18.0, wild-type (Wt) embryos were vascularized with a well-developed vascular plexus in the allantois (FIG. 3A) and had evidence of blood development (FIG. 5C). In contrast, ETV2 KO embryos showed clear developmental defects. Growth was retarded in ETV2 KOs relative to the Wt embryo, though both embryos were at the 24-somite stage (FIG. 5B), and lacked both blood and vascular lineages (FIG. 7C-H). ETV2 KO embryos lacked cardinal veins, dorsal aortae, and the endocardium, that are clearly developed in the Wt embryos (FIG. 5E-H).

Figure 1C:
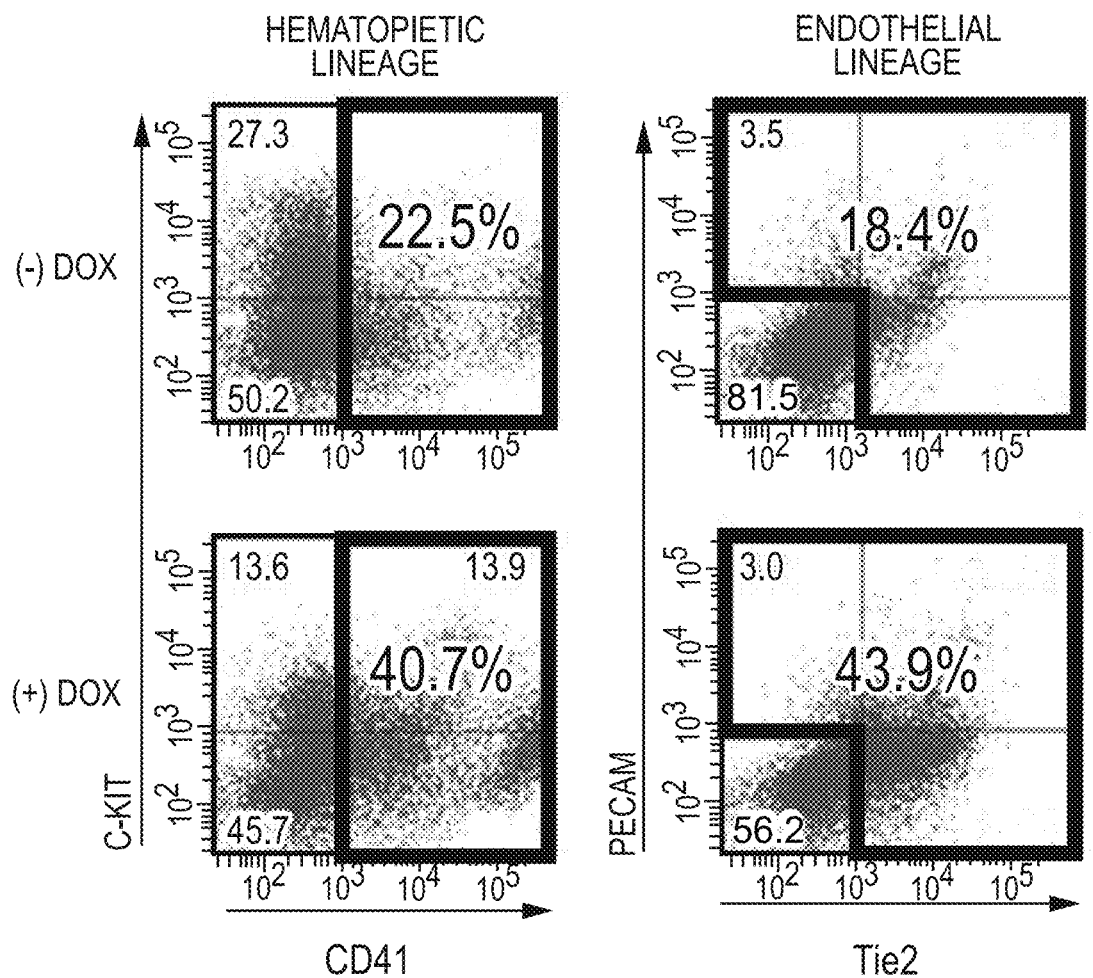
Figure 1D:
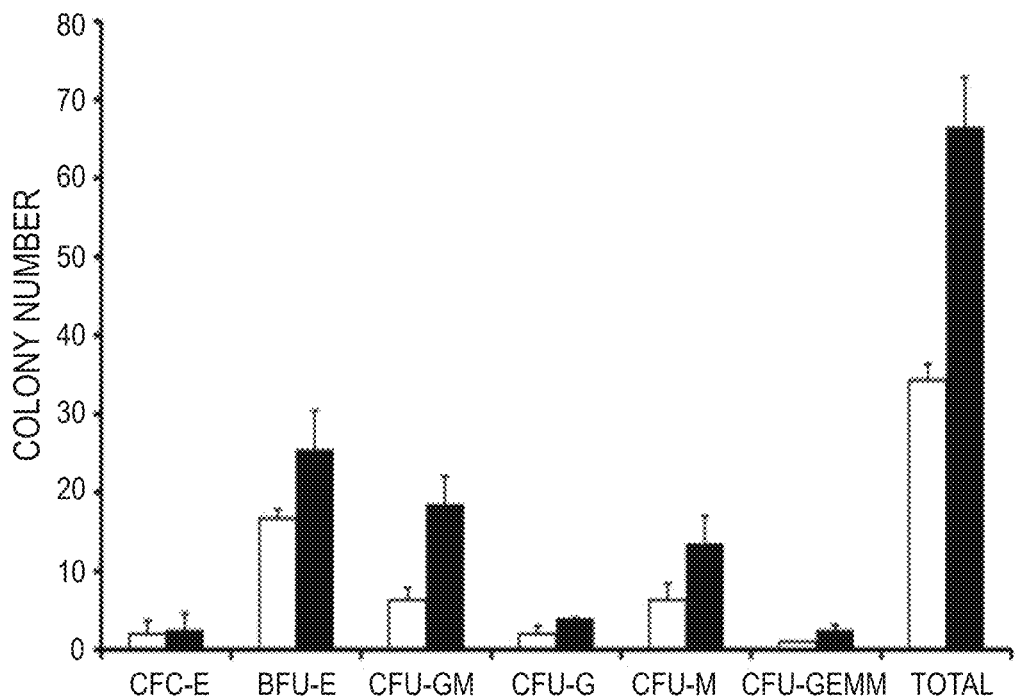

The results in FIGS. 1 and 5 reflect a similar phenotype and suggest that the function of ETV2 is conserved between mice and pigs. Further, these data demonstrate that one can direct multiple mutations into the porcine genome to support growth of chimeric organs that will be humanized in more than one cell type.

As an alternative to deleting ETV2, a mutation can be entered in to the gene, such as a frame shift mutation, wherein any protein produced would be non-functional. For example:

1) Frame-shift KO allele: In this example, a frame-shift is created in exon3 and a premature stop codon.
1) TALENs:

```
ETV2 3.1 (from 5' to 3')
Left:    TCATCCTTATCTGTCC      (SEQ ID NO: 11)

Right:   GCGGAGACCCAGTCC       (SEQ ID NO: 12)

ETV2 3.3 (from 5' to 3')
Left:    TACCGAACCCAGAAG       (SEQ ID NO: 13)

Right:   ACTGTGGGAGACACTCA     (SEQ ID NO: 14)
```

2) HDR Template:

ssETV2 3.1 HR-KO
(SEQ ID NO: 15)
cctccctaaactcagcttcatccttatctgtcccagggattc<u>*TAAGCTT*</u>c acagccggactgggtctccgcattaccgaacccagaagct lowercaseboldunderlined=ssETV2 3.1 cut site
UPPER CASE ITALICS=stop codon
Capital letters=inserted bases
Underlined=insertedHindIIIrestrictionsite ssETV2 3.3 WT sequence
(SEQ ID NO: 16)
cggactgggtctccgcattaccgaacccagaagctccatgGggcgcgggt gagtgtctcccacagtaactggaggtttcgatt <u>UPPERCASEBOLDUNDERLINED</u>=ssETV2 3.3 cut site ssETV2 3.3 HR-KO
(SEQ ID NO: 17)
cggactgggtctccgcattaccgaacccagaagctccatggg<u>*TAAGCTT*</u>gg cgcgggtgagtgtctcccacagtaactggaggtttcgatt lowercaseBOLDUNDERLINED=ssETV2 3.3 cut site
UPPER CASE ITALICS=stop codon
Capital letters=inserted bases
Underlined=insertedHindIIIrestrictionsite 3) Screening Primers:

ssETV2 E3 F4:   CACAACTCTCGTCCCGAACA (SEQ ID NO: 18)

ssETV2 E3 R4:   GAACGGACCCCAAGTGAGAG (SEQ ID NO: 19)

The Etv2 Mutant Embryos are Rescued by Wild-Type Mouse ES Cells.

The underlying assumption for generating humanized tissue in pigs is that the injected cells will preferentially populate the developmental niche in the mutant host and generate the missing cell types. As a proof-of-principle study and to evaluate whether Etv2 is an ideal target gene, mouse Etv2 mutant blastocysts were complemented with EYFP-labeled wild-type mouse ES cells (FIG. 6). To positively identify mutant alleles in the presence of wild-type cells, hemizygous mice of two distinct mutant lines of Etv2 were bred (unpublished data). Embryos were collected at E10.5 (one day later than the observed lethality of the Etv2 mutant embryo), genotyped and the distribution of EYFP positive cells and an endothelial marker, endomucin, were examined. In both Etv2 hemizygous and Etv2 mutant embryos, wild-type ES cells successfully integrated into the embryos (FIG. 6A, B). Immunohistochemical analysis revealed that EYFP-labeled wild-type cells randomly distributed to multiple cells types of all germ layers of hemizygous animals (FIG. 6C, E, G), whereas, in the Etv2 mutants, the majority of EYFP positive cells were found in the endothelial, endocardial and hematopoietic lineages (FIG. 6D, F. H). The data supported the notion that all endomucin positive endothelial cells expressed EYFP, indicating that they were derivatives from the wild-type ES cells (FIG. 6D, F, H). Etv2 mutant embryos also had EYFP-labeled Tie2-positive cells with primitive blood-like morphology inside the vessels, suggesting that the hematopoietic lineage is also rescued (data not shown).

Figure 8:
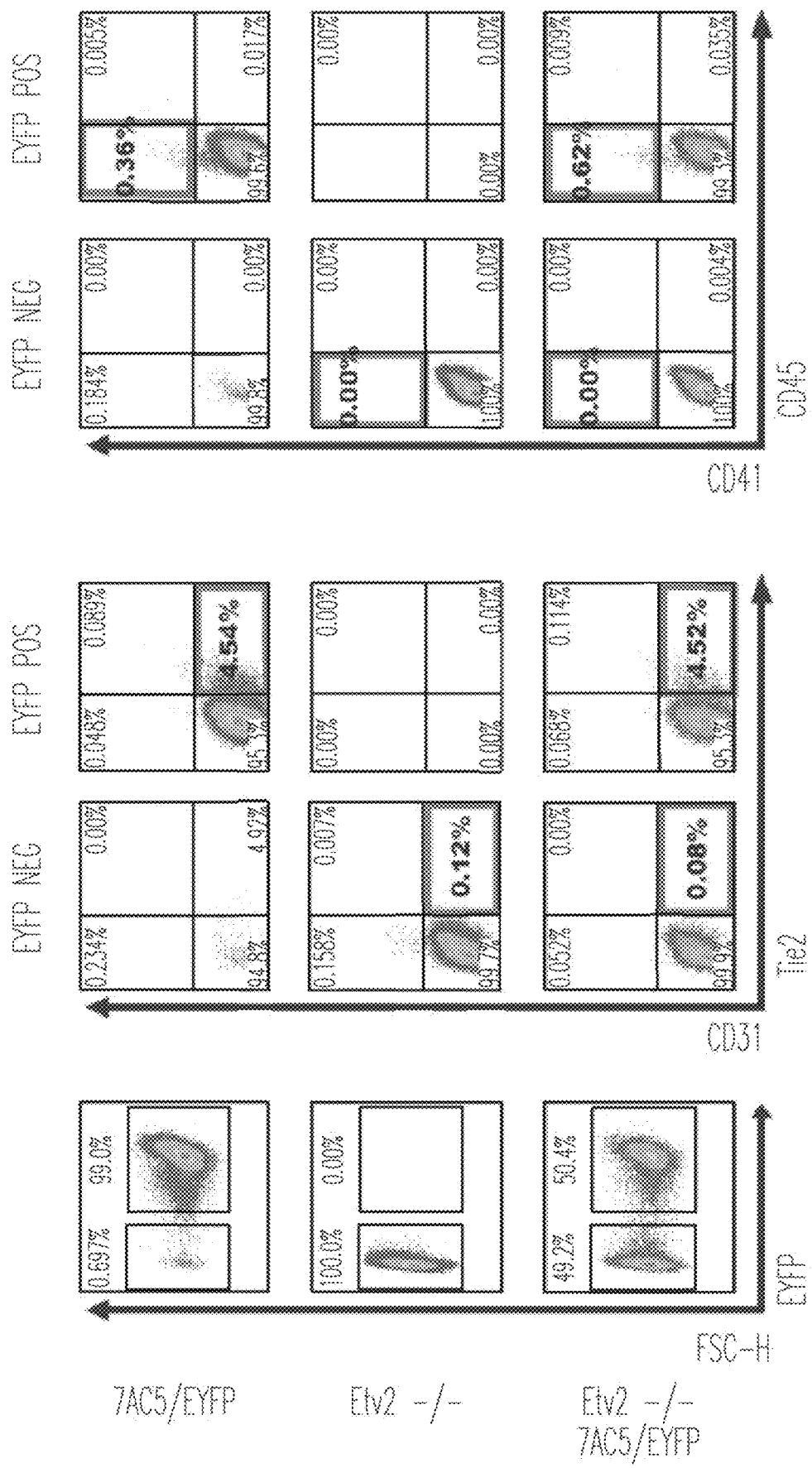
FIG. 8. Wild-type rat ES cells rescues the endothelial potential of Etv2 mutant mouse ES cells. Wild-type mouse ES cells, Etv2 mutant mouse ES cells, or Etv2 mutant mouse ES cells and wild-type rat ES cells at 1:1 ratio were induced to differentiate by EB formation. Note that wild-type mouse ES cells generate CD31$^+$ cells that line the vessel-like structures (A), which are missing in the mutant EBs (B). Co-differentiation with wild-type rat ES cells restored the CD31$^+$ population (C).

To further corroborate this finding, EYFP-labeled wild-type and Etv2 mutant ES cells were utilized (8), differentiated separately or together and examined the contribution of each line to the hematopoietic (CD41, CD45) and the endothelial (CD31, Tie2) lineages at day 4 of differentiation using FACS (FIG. 8). The wild-type 7AC5/EYFP cells were 99% EYFP positive, and generated 4.54% endothelial, 0.36% hematopoietic cells (upper row). Etv2 mutant cells were EYFP negative, and generated no endothelial and no hematopoietic cells (middle row). Analysis of co-differentiated EBs revealed that contribution of EYFP negative cells to the endothelial and hematopoietic lineages were indistinguishable from that of the Etv2 mutant ES cells, and EYFP positive cells generated the endothelial and hematopoietic lineages at a similar efficiency as wild type cells cultured alone (bottom row). This result indicated that "rescued" endothelial and hematopoietic lineages in the ES/EB co-differentiation system are derived exclusively from the wild-type ES cells. These results provide the rationale to target porcine ETV2 to generate the host animal for humanized endothelial and hematopoeitic lineages.

Rat Embryonic Stem Cells Rescue the Endothelial Populations in Etv2 Mutant Mouse Embryo Bodies.

Figures 7A, 7B, 7C:
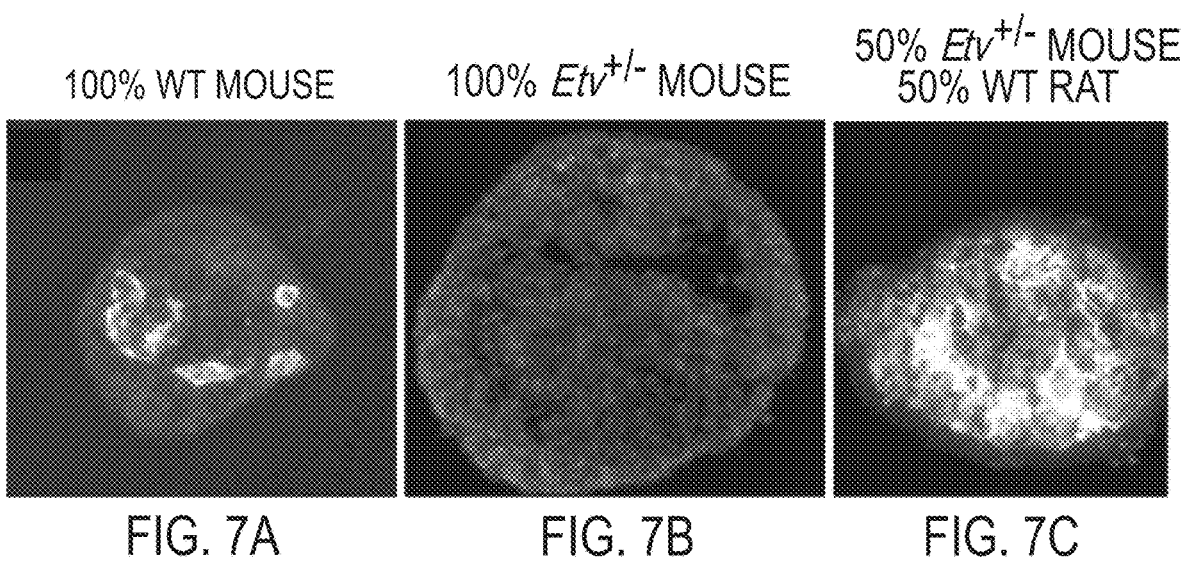
FIGS. 7A-C. Co-differentiation of Etv2 mutant and wild-type ES cells. 7AC5, EYFP-labeled otherwise wild-type ES cells and Etv2 mutant ES cells (Etv2$^{−/−}$) were either differentiated separately (top two rows) or mixed and co-differentiated (bottom row) by the hanging drop method. Cells were dissociated at day 4 and analyzed for cell surface markers. Note that EYFP negative Etv2 mutant cells do not contribute to the endothelial and hematopoietic lineages, indicating that there is minimal paracrine effect from the wild-type ES cells.

It was then tested whether complementation of the Etv2 null ES/EBs is possible using two different species. An in vitro ES/EB complementation assay was performed using Etv2 mutant mouse ES cells and wild-type rat ES cells (FIG. 7) (22). Wild-type or Etv2 mutant mouse ES cells were induced to differentiate by embryoid body (EB) formation by plating ES cells on ultra-low attachment plates in differentiation media. After 12 days of culture, EBs were fixed, sectioned and stained for an endothelial marker, CD31 (8). A strong CD31$^+$ population was observed lining the vessel-like structures in wild-type mouse EBs (FIG. 7A), but no CD31$^+$ cells were observed in the Etv2 mutant EBs (FIG. 7B). In contrast, co-differentiation cultures of Etv2 mutant ES cells and wild-type rat ES cells, revealed patches of cells with robust CD31 expression, indicating that CD31$^+$ population was rescued by this co-culture method (FIG. 7C). This success in mouse-rat complementation assay provides a proof-of-concept and the rationale to further progress to pig-pig and pig-human complementation experiments.

Human Umbilical Cord Blood Stem Cells (hUCBSC) and hiPSC Integrate into the Inner Cell Mass (ICM) of Porcine Parthenotes (Embryos Electrically Activated to Develop without Fertilization).

Figures 9A, 9B:
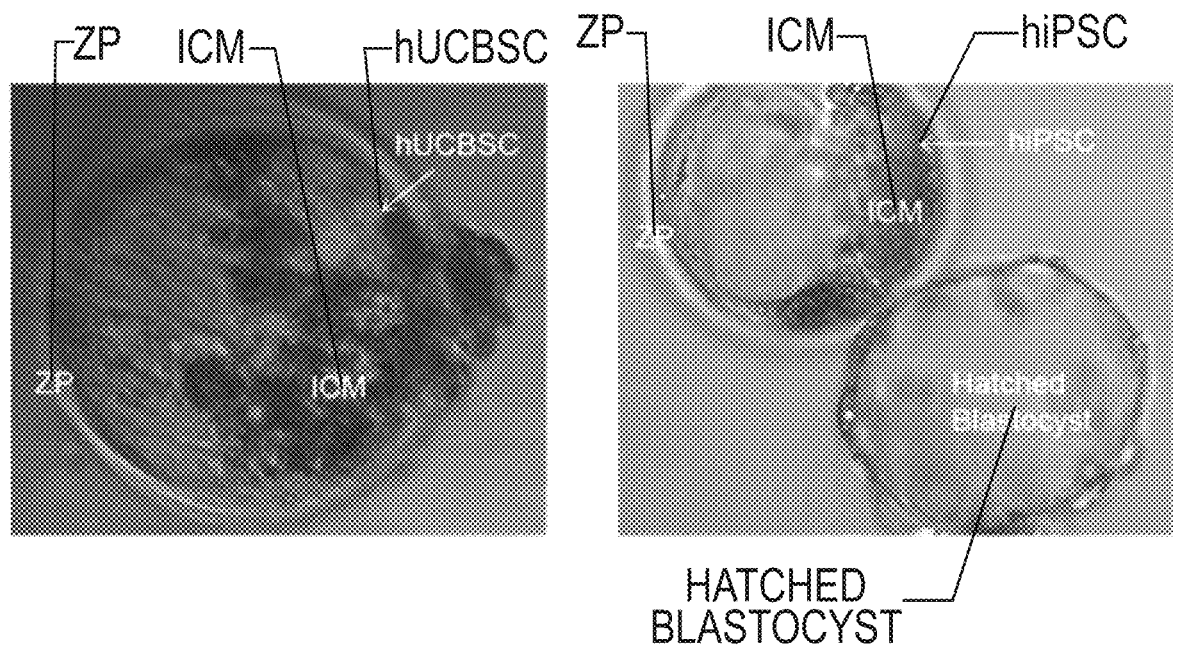
FIG. 9A-B. Chimeric human-porcine blastocysts. (A) Blastocyst with hUCBSCs in the ICM. Note that the blastocyst is beginning to hatch. (B) Blastocyst with DiI-labeled hiPSCs in the ICM. Note adjacent hatched blastocyst with DiI-labeled hiPSCs. ZP: zona pellucida; ICM: inner cell mass.

To evaluate the feasibility of the strategy to generate human-pig chimeras, the capacity of hUCBSC and hiPSC to integrate into the porcine blastocysts and participate in embryonic development was examined. Porcine parthenogenetic blastocysts were generated using electrical stimulation of oocytes (42). Six days following activation 9-12 DiI- or EdU (24 hr)-labeled hUCBSC or hiPSC were injected into the blastocoel cavity. Blastocysts were allowed to recover two days in culture and then imaged. Labeled hUCBSCs and hiPSCs were observed in the ICM of 90% of the porcine blastocysts (FIG. 9A, B, representative images are shown). Comparison of DiI distribution with immunohistochemistry using human nuclear antigen-specific antibody (HNA) reveals that HNA antibody detects injected human stem cells (FIG. 9A, arrows). Blastocysts injected with EdU labeled hiPSC were further pulsed with BrdU for 1 hour before harvest to detect proliferating cells. Double labeling with EdU reveals that injected human stem cells continued to proliferate after 48 hrs of injection (FIG. 9B, arrows). These results demonstrate the incorporation of human stem cells into the ICM of porcine blastocysts, and the developmental progression of the chimeric blastocysts to the hatching stage in preparation for implantation into the uterus. To examine the integration of human stem cells into porcine parthenogenetic embryos, the chimeric blastocysts were transplanted into pseudopregnant sows and analyzed embryos at E28. Normal developing embryos were obtained as previously reported (30), one of which was found to contain a cluster of human cells that stained with the HNA antibody. These results support and provide a rapid assay to examine whether human stem cell populations are compatible and/or contribute to the ICM development. Furthermore, implantation of parthenogenetic blastocysts provides a high-throughput method to examine integration and differentiation of human stem cells into developing embryos. A significant advantage of this strategy is that porcine oocytes are abundantly available as a bi-product of food production, and parthenogenetic embryos can be generated in large quantities on a regular basis. It should be noted that parthenogenetic embryos do not survive past 8 weeks, and therefore negates the concern of inadvertently giving birth to undesired human-porcine chimeras.

BIBLIOGRAPHY

1. Garry, D J, et al. Circ Res. 2004; 95(9):852-4.
2. Hoffman, J I. Pediatr Cardiol. 1995; 16(3):103-13.
3. Rasmussen, T L, et al. Circulation. 2011; 123(16):1771-9.
4. De Val, S, et al. Cell. 2008; 135(6):1053-64.
5. Lee, D, et al. Cell Stem Cell. 2008:2(5):497-507. PMCID: 2683414.
6. Ferdous, A, et al. Natl Acad Sci USA. 2009; 106(3):814-9. PMCID: 2630085.
7. Kataoka, H, et al. Blood. 2011.
8. Lee, D. et al. Stem Cells. 2011; 29(3):539-48.
9. Rasmussen, T L, et al. Development. 2011; 138(21):4801-12. PMCID: 3190388.
10. Koyano-Nakagawa, N, et al. Stem Cells. 2012; 30(8):1611-23. PMCID: 3651838.
11. Rasmussen, T L, et al. PLoS One. 2012; 7(11):e50103. PMCID: 3501484.
12. Behrens, A N, et al. Submitted to Developmental Biology. 2013.
13. Chan, S S, et al. Cell Stem Cell. 2013; 12(5):587-601. PMCID: 3646300.
14. Kataoka, H, et al. Exp Hematol. 2013; 41(6):567-81 e9.
15. Kobayashi, K, et al. Genes Cells. 2013; 18(8):704-21.
16. Rasmussen, T L et al. Genesis. 2013:51(7):471-80.
17. Shi, X, et al. Dev Biol. 2014; 389(2):208-18.
18. Carlson, D F, et al. Proc Natl Acad Sci USA. 2012; 109(43): 17382-7. PMCID: 3491456.
19. Tan, W, et al. Proc Natl Acad Sci USA. 2013.
20. Xin. J, et al. PLoS One. 2013; 8(12):e84250. PMCID: 3866186.
21. Kure-bayashi, S, et al. Theriogenology. 2000; 53(5):1105-19.
22. Caprioli, A, et al. Circulation. 2011; 123(15):1633-41. PMCID: 3110259.
23. Borges, L. et al. Blood. 2012; 119(23):5417-28.
24. Behrens, A N, et al. Stem Cells and Development. 2013; 22(15):2211-20. PMCID: 3715789.
25. Borges, L, et al. Stem Cells. 2013; 31(9):1893-901. PMCID: 3795927.
26. Roger, V L, et al. Circulation. 2012:125(1):188-97.
27. Kobayashi, T, et al. Cell. 2010; 142(5):787-99.
28. Bort, R. eat 1. Dev Biol. 2006; 290(1):44-56.
29. Isotani, A, et al. Genes Cells. 2011; 16(4):397-405.
30. Usui, J, et al. Am J Pathol. 2012; 180(6):2417-26.
31. Matsunari, H, et al. Proc Natl Acad Sci USA. 2013; 110(12):4557-62. PMCID: 3607052.
32. Liu, F, et al. Blood. 2012; 119(14):3295-305. PMCID: 3321855.
33. Milland, J, et al. Immunology and cell biology. 2005; 83(6):687-93.
34. Carlson, D F, et al. Transgenic Res. 2011; 20(5):1125-37.
35. Carlson, D F, et al. Transgenic Res. 2011:20(1):29-45. PMCID: 3516389.
36. Men, H, et al. PLoS One. 2013; 8(2):e56518. PMCID: 3577902.
37. Li, P, et al. Cell. 2008; 135(7):1299-310. PMCID: 2735113.

38. Hill, M A. Embryology *Carnegie Stage Comparison*. [Website]; 2014 [updated 2014; cited]; Available from: http://embryology.med.unsw.edu.au/embryology/index.php?title=Carnegie_Stage_Comparison.
39. Adamo, L, Garcia-Cardena, G. Dev Biol. 2011; 362(1): 1-10.
40. Swiers, G, de Bruijn, M, Speck, Int J Dev Biol. 2010; 54(6-7):1151-63.
41. Alishahi, A, et al. Dev Dyn. 2009; 238(8):2095-102. PMCID: 2742708.
42. Heinz, M, et al. Exp Hematol. 2002; 30(7):809-15.
43. Piriou-Guzylack, L, Salmon, H. Veterinary research. 2008:39(6):54.
44. Nakano, K, PLoS One. 2013; 8(4):e61900. PMCID: 3633951.
45. King, T J, et al. Reproduction. 2002:123(4):507-15.
46. Zhu, J, et al. Cloning Stem Cells. 2003; 5(4):355-65.
47. Gerhardt, H, et al. J Cell Biol. 2003; 161(6):1163-77. PMCID: 2172999.
48. Masino, A M, et al. Circ Res. 2004; 95(4):389-97.
49. Inoue, K. Shiga, T, Ito, Y. Neural development. 2008; 3:20. PMCID: 2531103.
50. Herberth, B, et al. International Society for Developmental Neuroscience. 2005; 23(5):449-63.

The invention is described with reference to various specific and preferred embodiments and techniques. However, it should be understood that many variations and modifications may be made while remaining within its scope. All referenced publications, patents and patent documents are intended to be incorporated by reference, as though individually incorporated by reference.

What is claimed is:

1. A genetically modified isolated Sus scrofa pig cell, morula or blastocyst whose genome comprises a homozygous deletion of an endogenous ETV2 gene, wherein the cell, morula or blastocyst lacks functional endogenous ETV2 protein.

* * * * *